US008317859B2

(12) United States Patent
Snow et al.

(10) Patent No.: US 8,317,859 B2
(45) Date of Patent: Nov. 27, 2012

(54) DEVICES AND METHODS FOR CONTROLLING EXPANDABLE PROSTHESES DURING DEPLOYMENT

(75) Inventors: David W. Snow, San Carlos, CA (US); Timothy W. Robinson, Sandown, NH (US); Dawn M. Henderson, Lowell, MA (US); Stuart Lin, Mountain View, CA (US)

(73) Assignee: J.W. Medical Systems Ltd., Weihai Shandong (CN)

( * ) Notice: Subject to any disclaimer, the term of this patent is extended or adjusted under 35 U.S.C. 154(b) by 1096 days.

(21) Appl. No.: 11/752,448

(22) Filed: May 23, 2007

(65) Prior Publication Data

US 2008/0132989 A1    Jun. 5, 2008

Related U.S. Application Data

(63) Continuation-in-part of application No. 10/957,079, filed on Sep. 30, 2004, now abandoned, which is a continuation-in-part of application No. 10/879,949, filed on Jun. 28, 2004, now abandoned.

(51) Int. Cl.
*A61F 2/06* (2006.01)
(52) U.S. Cl. ....................................... 623/6.12
(58) Field of Classification Search ................. 623/1.11, 623/1.12, 1.23; 606/108, 194
See application file for complete search history.

(56) References Cited

U.S. PATENT DOCUMENTS

| 4,069,825 | A | 1/1978 | Akiyama |
| 4,468,224 | A | 8/1984 | Enzmann et al. |
| 4,512,338 | A | 4/1985 | Balko |
| 4,564,014 | A | 1/1986 | Fogarty et al. |
| 4,580,568 | A | 4/1986 | Gianturco |
| 4,681,110 | A | 7/1987 | Wiktor |
| 4,690,684 | A | 9/1987 | McGreevy et al. |
| 4,733,665 | A | 3/1988 | Palmaz |
| 4,739,762 | A | 4/1988 | Palmaz |

(Continued)

FOREIGN PATENT DOCUMENTS

DE    1 953 1659    3/1997

(Continued)

OTHER PUBLICATIONS

International Search Report and Written Opinion of PCT Application No. PCT/US2008/061041, mailed Nov. 7, 2008, 13 pages total.

(Continued)

*Primary Examiner* — Katherine Dowe
(74) *Attorney, Agent, or Firm* — Kilpatrick Townsend & Stockton LLP

(57) ABSTRACT

Prosthesis delivery devices and methods are provided that enable precise control of prosthesis position during deployment. The catheter for delivering a prosthesis to a treatment site in a body lumen typically carries one or more self-expanding tubular prostheses within a sheath. A radially expandable control member is positionable within the prostheses and has an expanded shape which engages an inner surface of the prostheses to urge the prostheses outwardly against the sheath. The radially expandable control member therefore controls axial position of the prostheses during deployment. Thus one or more prostheses may be deployed at a treatment site precisely. When multiple prostheses are deployed, excessive spacing or overlap between adjacent prostheses is minimized. The prostheses of the present invention are often deployed in stenotic lesions in peripheral arteries as well as coronary arteries and other body lumens.

74 Claims, 17 Drawing Sheets

U.S. PATENT DOCUMENTS

| | | |
|---|---|---|
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A * | 2/2000 | Stanford .................. 606/198 |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |

| Patent No. | Date | Inventor |
|---|---|---|
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 * | 1/2004 | Belding et al. ............... 623/1.11 |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Betelia et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,913,619 B2 | 7/2005 | Brown et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 * | 2/2007 | Gilson ........................ 623/1.11 |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |

| | | |
|---|---|---|
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,534,449 B2 | 5/2009 | Saltzman et al. |
| 7,699,886 B2 | 4/2010 | Sugimoto |
| 7,918,881 B2 | 4/2011 | Andreas et al. |
| 7,993,388 B2 | 8/2011 | Lee et al. |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0037358 A1 | 3/2002 | Barry et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1* | 1/2004 | Armstrong et al. .......... 623/1.12 |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1* | 6/2005 | Griffin ........................ 606/198 |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1* | 12/2005 | Peckham ..................... 623/1.11 |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |

| | | | |
|---|---|---|---|
| 2008/0097299 A1 | 4/2008 | Andreas et al. | |
| 2008/0097574 A1 | 4/2008 | Andreas et al. | |
| 2008/0125850 A1 | 5/2008 | Andreas et al. | |
| 2008/0147162 A1 | 6/2008 | Andreas et al. | |
| 2008/0177369 A1 | 7/2008 | Will et al. | |
| 2008/0199510 A1 | 8/2008 | Ruane et al. | |
| 2008/0208311 A1 | 8/2008 | Kao et al. | |
| 2008/0208318 A1 | 8/2008 | Kao et al. | |
| 2008/0234795 A1 | 9/2008 | Snow et al. | |
| 2008/0234798 A1 | 9/2008 | Chew et al. | |
| 2008/0234799 A1 | 9/2008 | Acosta et al. | |
| 2008/0243225 A1 | 10/2008 | Satasiya et al. | |
| 2008/0249607 A1 | 10/2008 | Webster et al. | |
| 2008/0269865 A1 | 10/2008 | Snow et al. | |
| 2009/0076584 A1 | 3/2009 | Mao et al. | |
| 2009/0105686 A1 | 4/2009 | Snow et al. | |
| 2009/0149863 A1 | 6/2009 | Andreas et al. | |
| 2009/0234428 A1 | 9/2009 | Snow et al. | |
| 2009/0248137 A1 | 10/2009 | Andersen et al. | |
| 2009/0248140 A1 | 10/2009 | Gerberding | |
| 2009/0264979 A1 | 10/2009 | Kao et al. | |
| 2010/0004729 A1 | 1/2010 | Chew et al. | |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 | 6/1996 |
| EP | 0 797 963 A2 | 10/1997 |
| EP | 0 947 180 | 10/1999 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 | 6/2003 |
| EP | 1 523 959 A2 | 4/2005 |
| EP | 1 523 960 A2 | 4/2005 |
| GB | 2277875 A | 11/1994 |
| JP | 03-133446 | 6/1991 |
| JP | 10-503663 | 4/1998 |
| JP | 10-295823 | 11/1998 |
| JP | 2001-190687 | 7/2001 |
| JP | 2004-121343 A | 4/2004 |
| WO | 94/27667 A1 | 12/1994 |
| WO | WO 95/26695 A2 | 10/1995 |
| WO | WO 96/33677 | 10/1996 |
| WO | 96/37167 A1 | 11/1996 |
| WO | WO 96/39077 | 12/1996 |
| WO | WO 97/46174 | 12/1997 |
| WO | WO 97/48351 | 12/1997 |
| WO | WO 98/37833 | 9/1998 |
| WO | WO 99/01087 A2 | 1/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | 00/51525 A1 | 9/2000 |
| WO | WO 00/56237 | 9/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | WO 2005/009295 | 2/2005 |
| WO | WO 2005/013853 | 2/2005 |
| WO | WO 2007/053187 | 5/2007 |
| WO | WO 2007/146411 | 12/2007 |
| WO | WO 2008/005111 | 1/2008 |

OTHER PUBLICATIONS

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

"Drug Delivery Stent With Holes Located on Neutral Axis" Research Disclosure, Kenneth Mason Publications, Hampshire, CB, No. 429, Jan. 2000, p. 13.

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com, (2003).

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; abandoned.

U.S. Appl. No. 10/874,859, filed Jun. 22, 2004, first named inventor: Pablo Acosta. Abandoned.

U.S. Appl. No. 11/462,951, filed Aug. 7, 2006, first named inventor: David Snow.
U.S. Appl. No. 11/689,927, filed Mar. 22, 2007, first named inventor: David Snow.
U.S. Appl. No. 11/771,929, filed Jun. 29, 2007, first named inventor: David Snow.
U.S. Appl. No. 11/857,562, filed Sep. 19, 2007, first named inventor: Bryan Mao.
U.S. Appl. No. 11/938,730, filed Nov. 12, 2007, first named inventor: Sunmi Chew; abandoned.
U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
U.S. Appl. No. 12/043,513, filed Mar. 6, 2008, first named inventor: David Lowe.
U.S. Appl. No. 12/057,527, filed Mar. 28, 2008, first named inventor: Allan Will.
U.S. Appl. No. 12/061,951, filed Apr. 3, 2008, first named inventor: Stephen Kao.
U.S. Appl. No. 12/109,477, filed Apr. 25, 2008, first named inventor: Stephen Kao.
U.S. Appl. No. 12/127,147, filed May 27, 2008, first named inventor: Sunmi Chew.
U.S. Appl. No. 12/133,909, filed Jun. 5, 2008, first named inventor: David Sanderson.

* cited by examiner

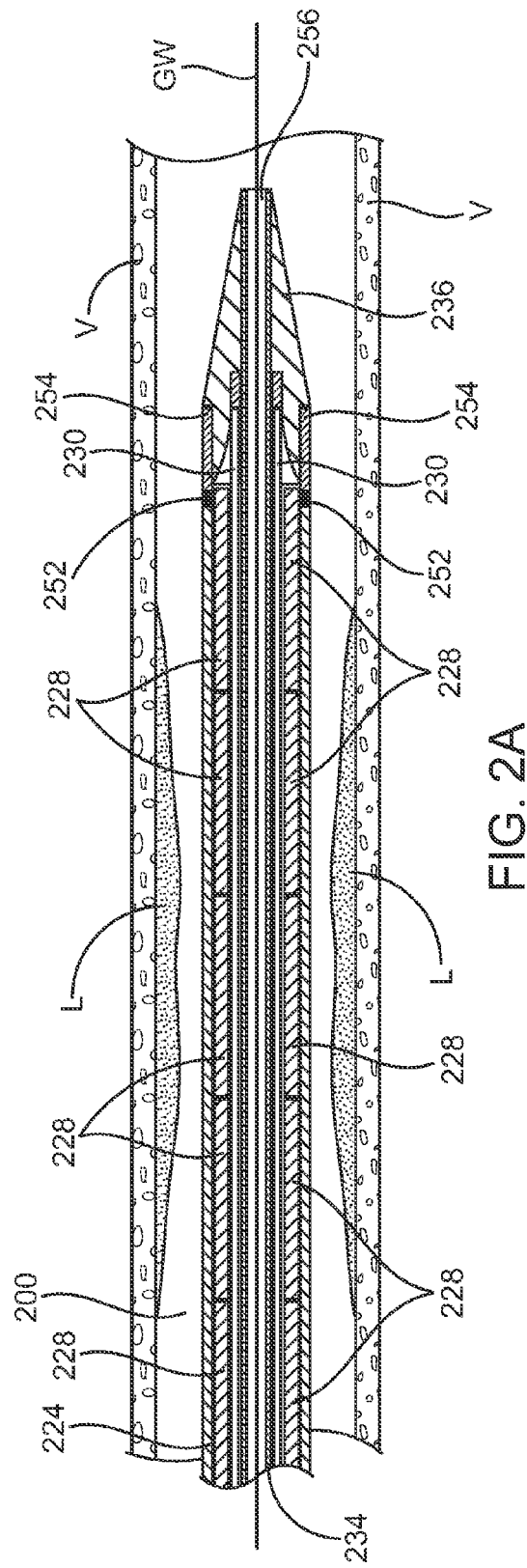
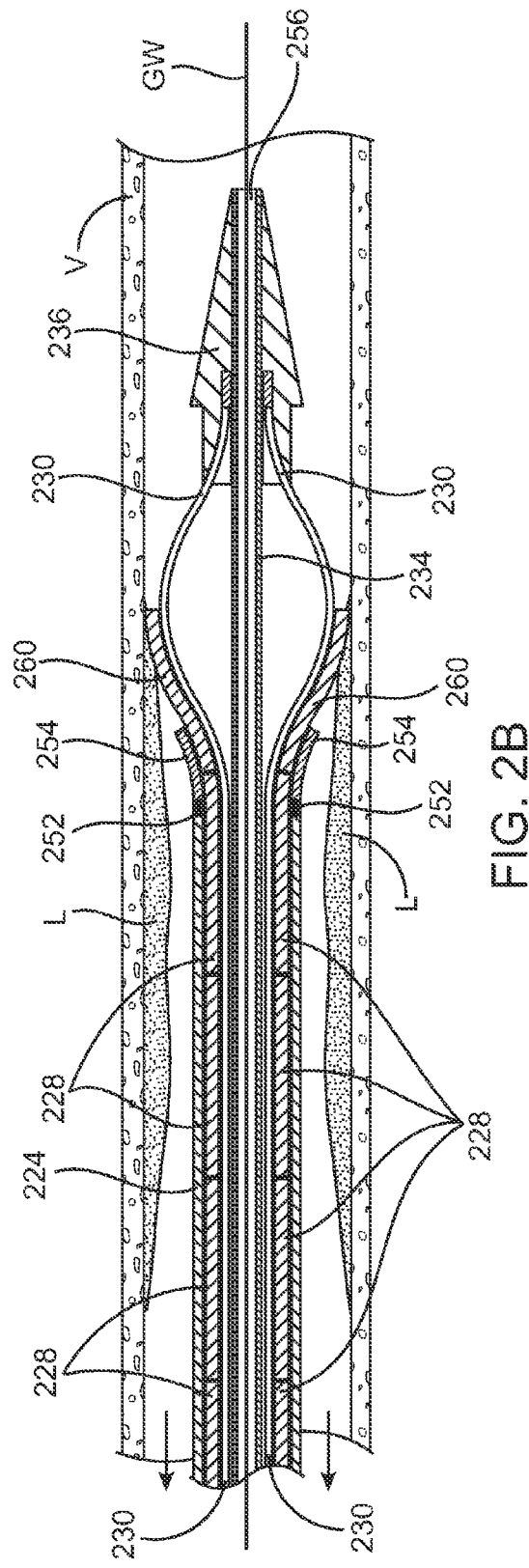
FIG. 2A
FIG. 2B

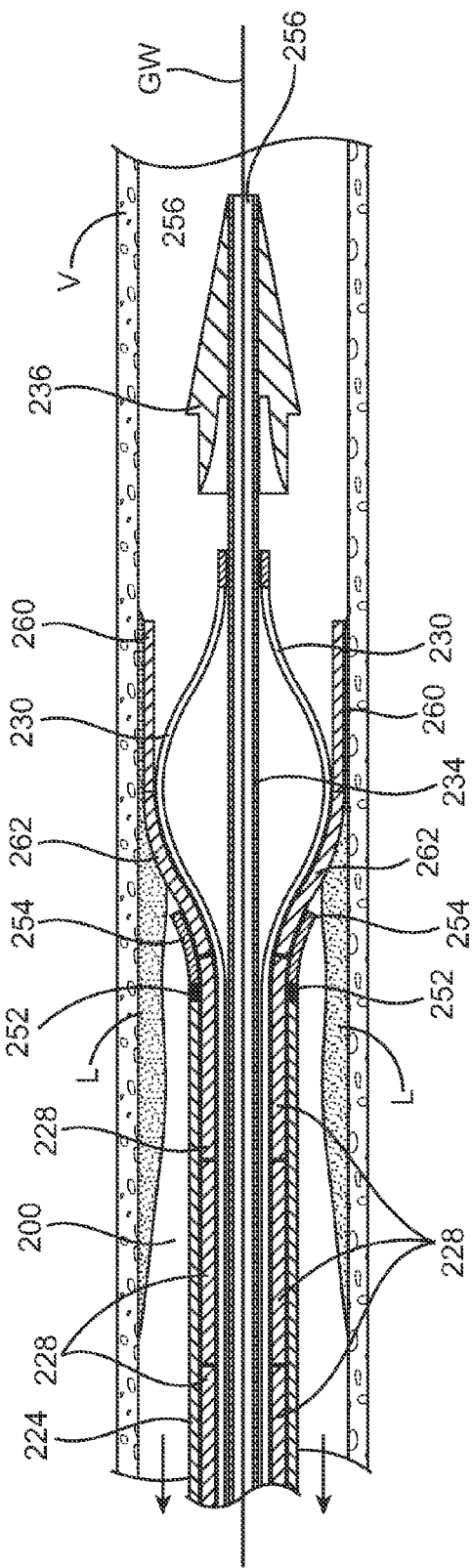
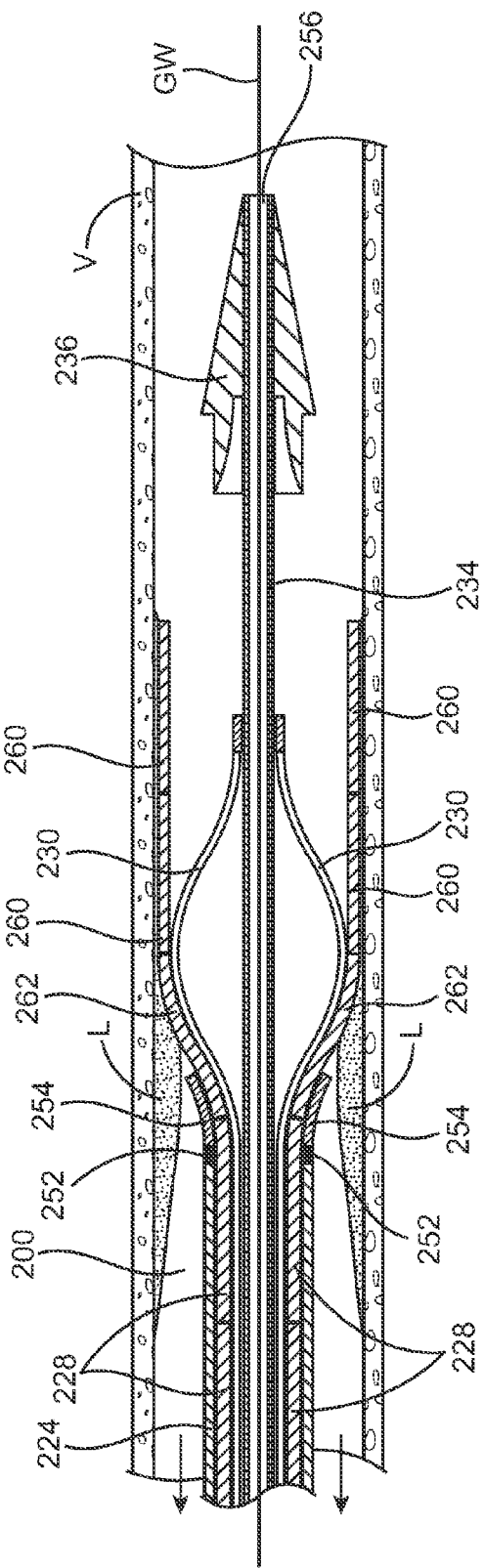
FIG. 2C
FIG. 2D

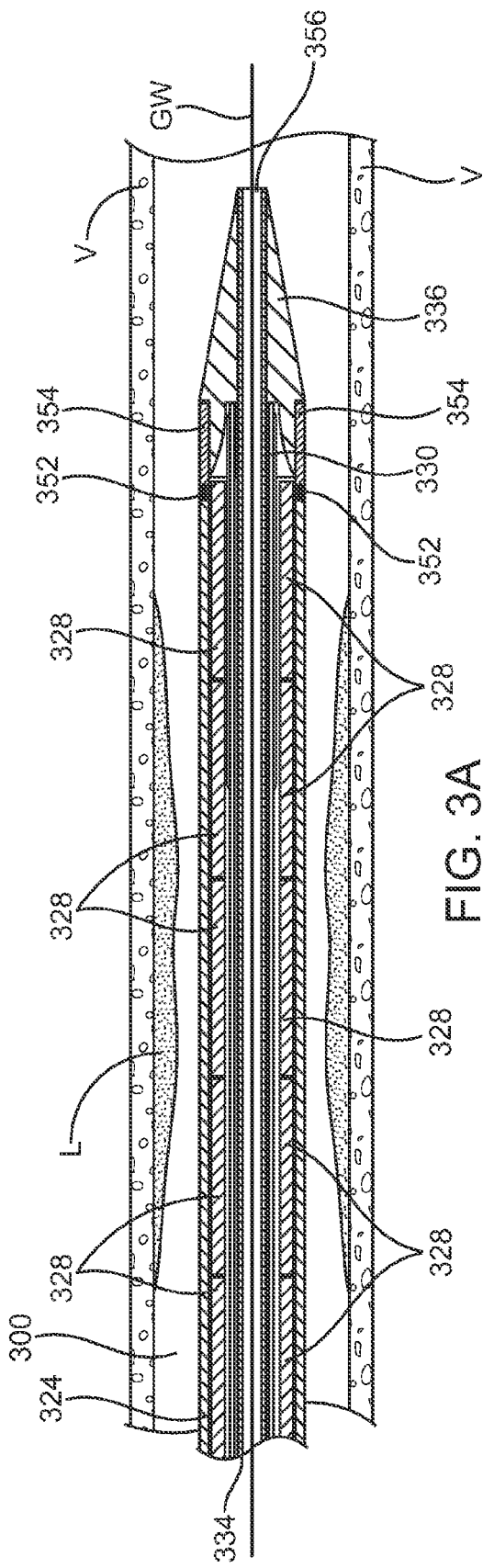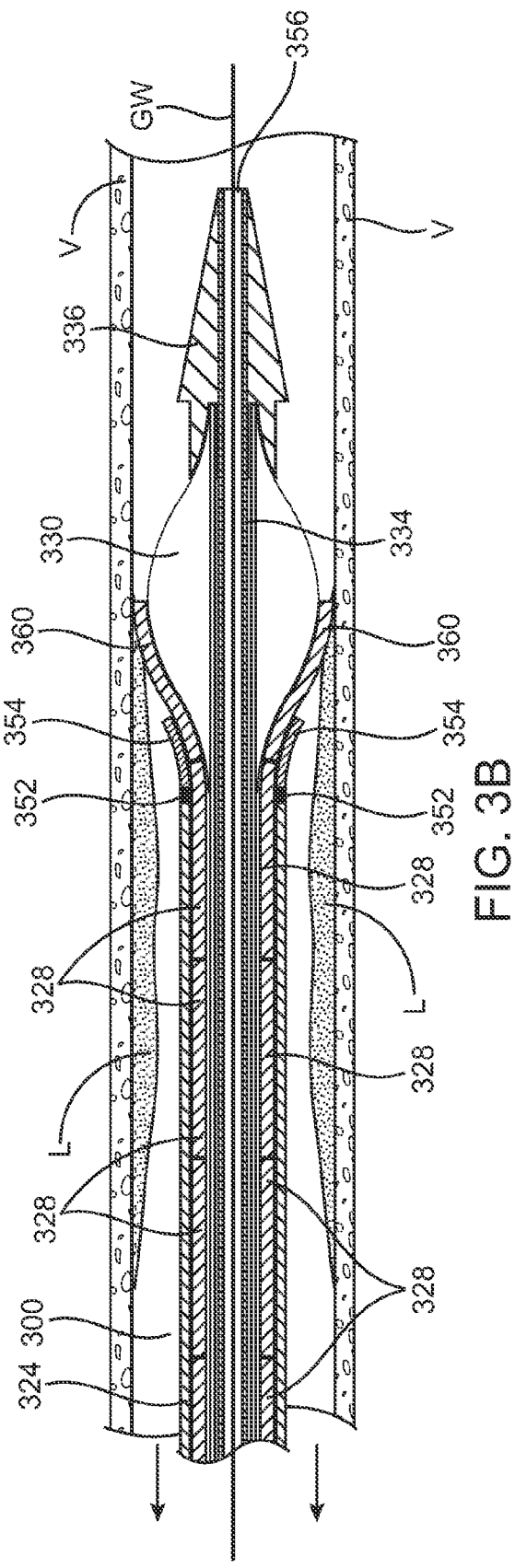
FIG. 3A
FIG. 3B

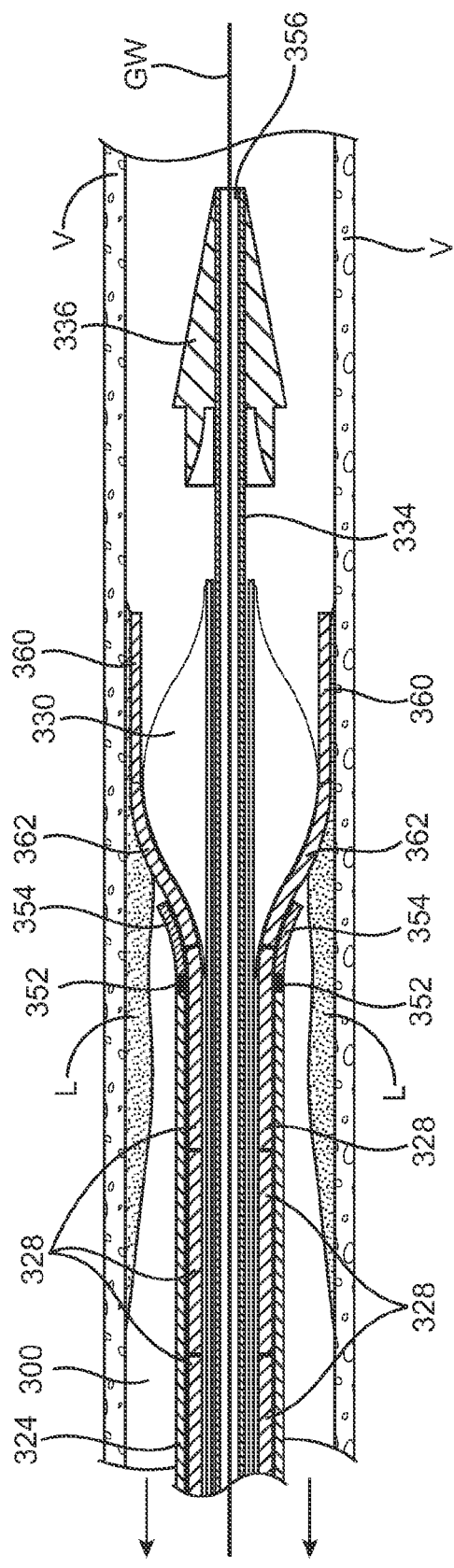
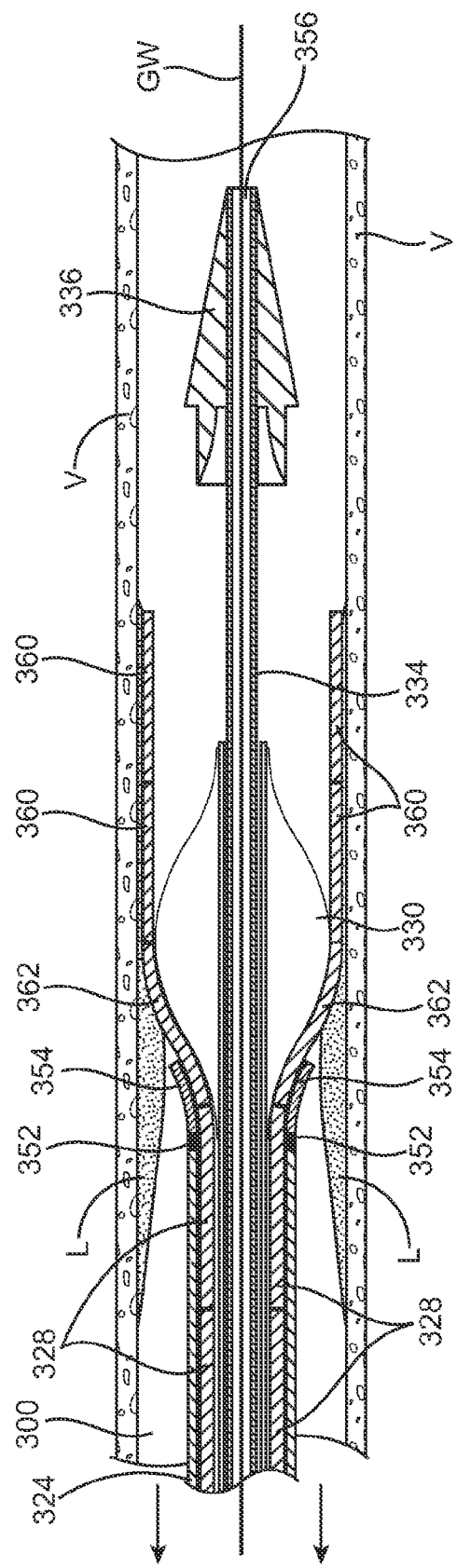
FIG. 3C
FIG. 3D

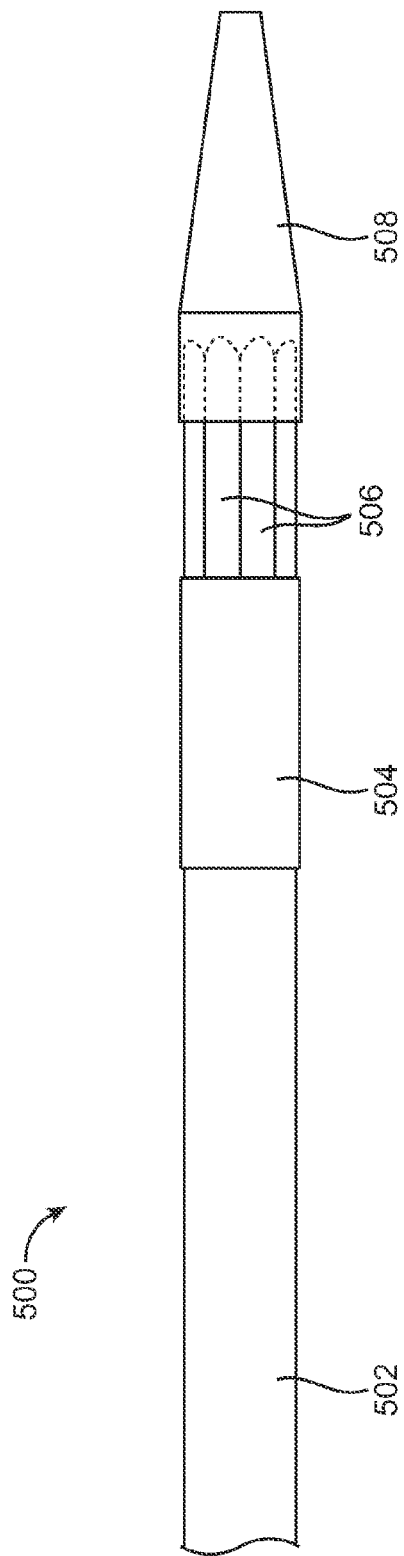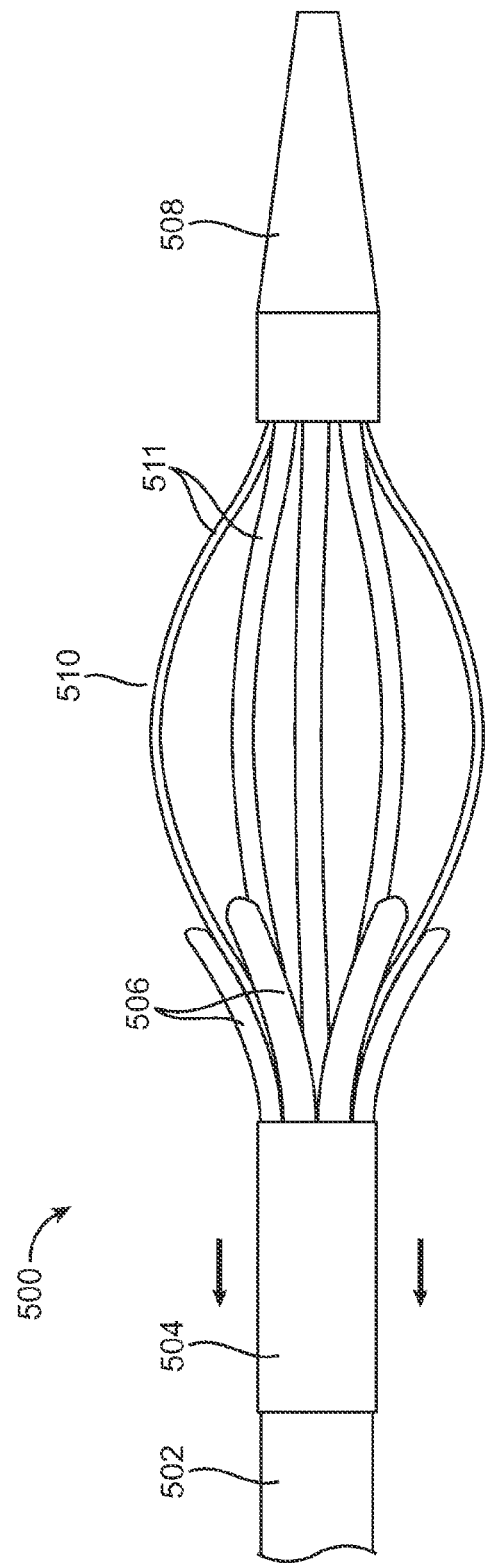
FIG. 5A
FIG. 5B

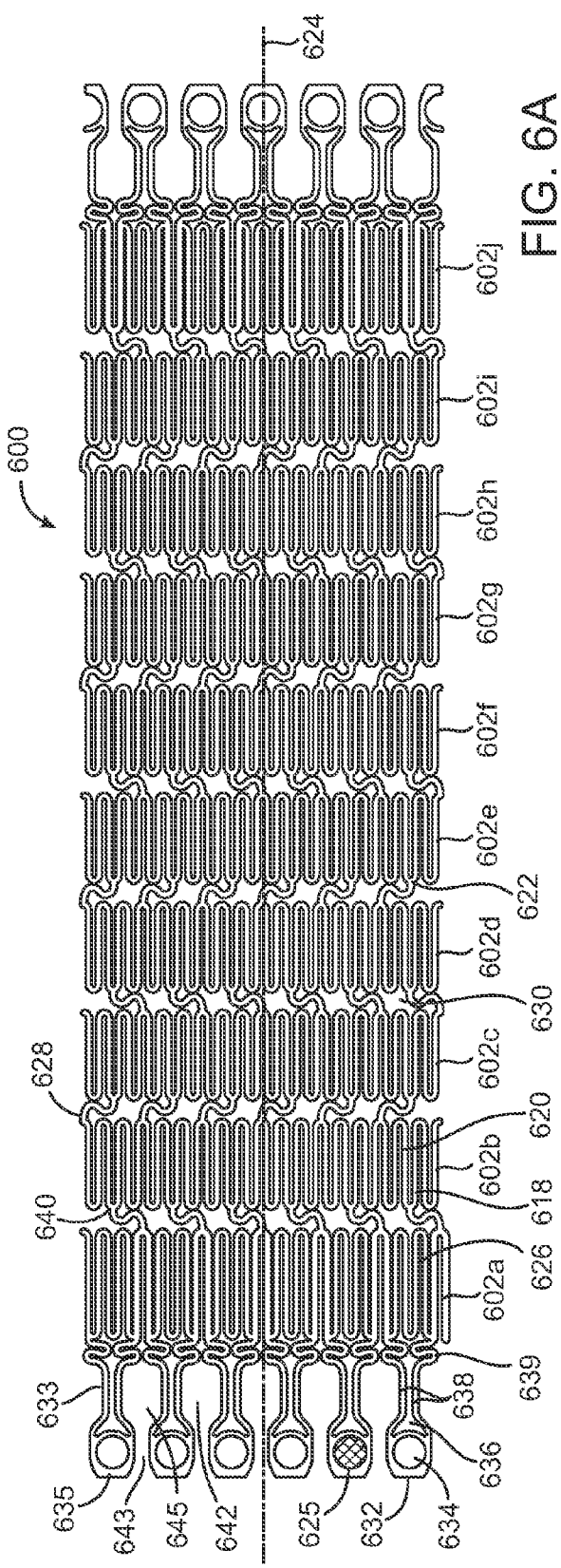
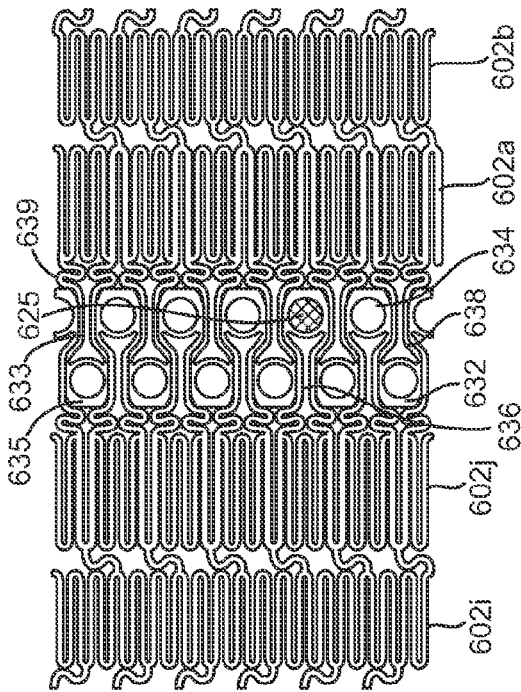
FIG. 6A
FIG. 6B

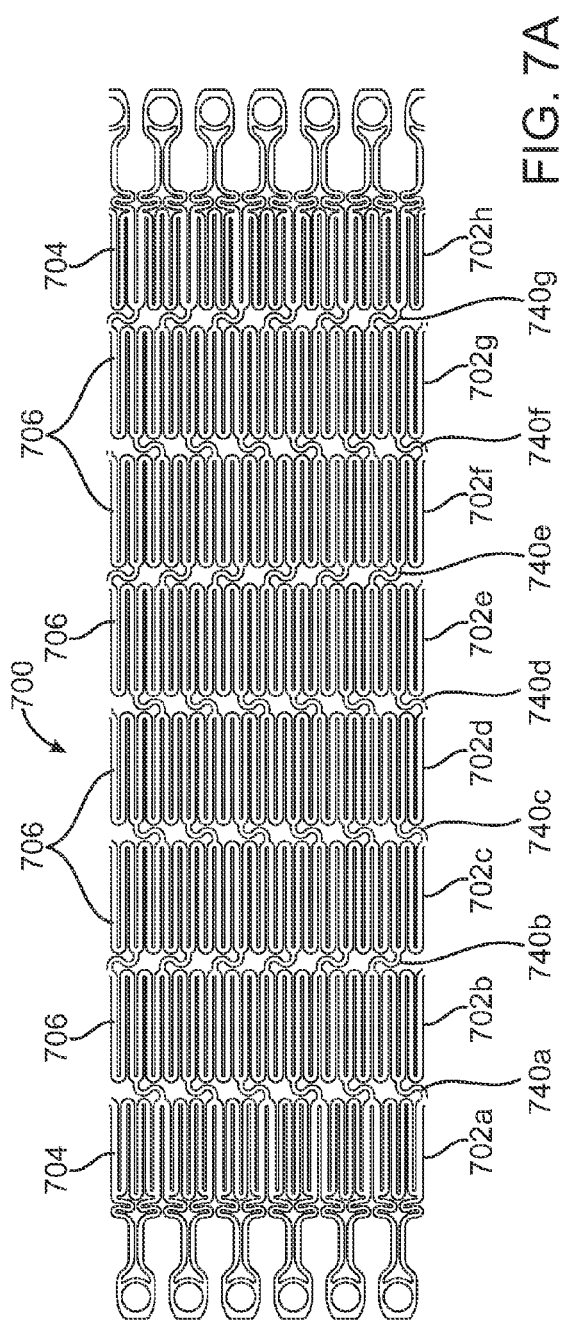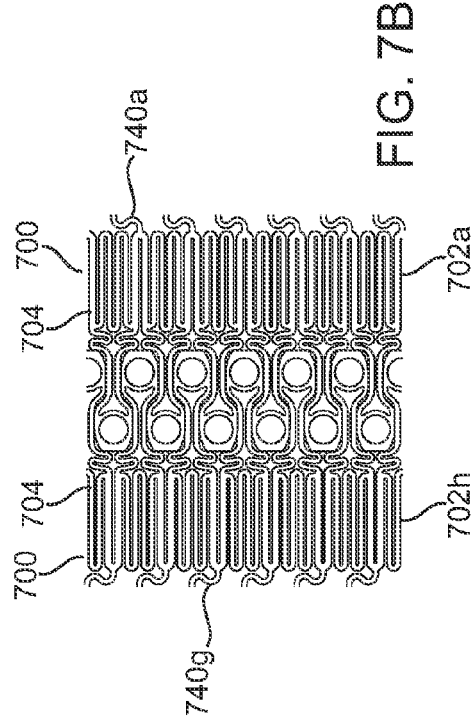

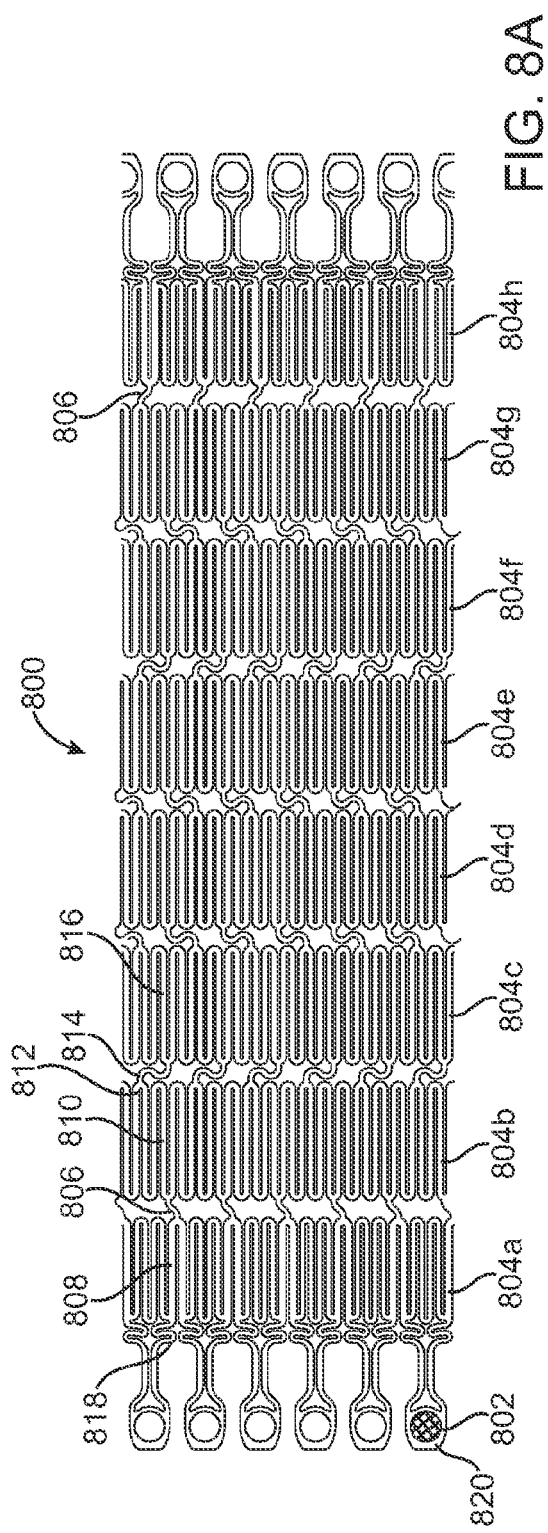
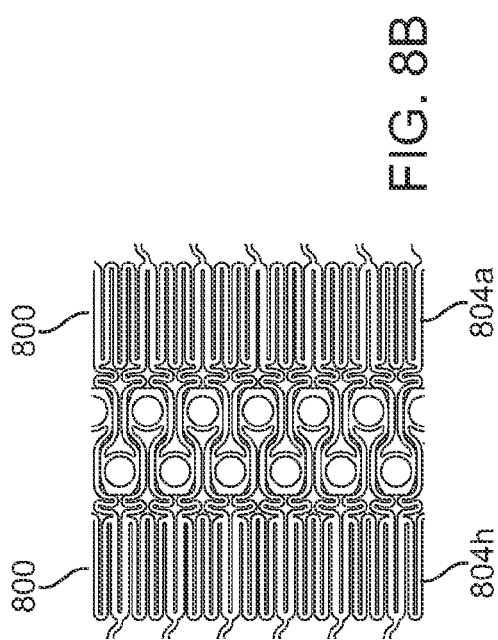
FIG. 8A
FIG. 8B

DEVICES AND METHODS FOR CONTROLLING EXPANDABLE PROSTHESES DURING DEPLOYMENT

CROSS-REFERENCES TO RELATED APPLICATIONS

The present application is a continuation-in-part of U.S. patent application Ser. No. 10/957,079, filed Sep. 30, 2004, now abandoned, which is a continuation-in-part of U.S. patent application Ser. No. 10/879,949, filed Jun. 28, 2004, now abandoned, the full disclosures of which are hereby incorporated by reference.

BACKGROUND OF THE INVENTION

1. Field of the Invention

This invention relates generally to medical apparatus and methods, and more specifically to vascular catheters, stents and stent delivery systems for use in the coronary and peripheral arteries as well as other vessels and body lumens.

Stenting is an important treatment option for patients with vascular occlusive disease. The stenting procedure involves placing a tubular prosthesis at the site of a lesion, typically within a diseased artery. The procedure is performed in order to maintain the patency of the artery and is often performed after a primary treatment such as angioplasty. Early stent results suffered from high rates of restenosis, i.e. the tendency for the stented artery to become re-occluded following implantation of the stent. However, in recent years, restenosis rates have decreased substantially, due in part to drug eluting stents as well as other improvements in stent delivery methods and stent technology. As a result, the number of stent related procedures being performed worldwide continues to dramatically increase.

Stents are typically either self-expanding or balloon expandable and they are delivered to the arteries using long, flexible vascular catheters typically inserted percutaneously through the patient's femoral artery. For balloon expandable stents, the stents are usually mounted over a balloon on the delivery catheter, thus, when the balloon is inflated, the balloon expands and correspondingly expands and deforms the stent to the desired diameter. The balloon can then be deflated and removed, leaving the stent in place. For self-expanding stents, the stent is simply released from the delivery catheter so that it resiliently expands into engagement with the vessel wall. Self-expanding stents are often used in the peripheral vascular system since they are more resilient than balloon expandable stents. Resilient stents are better suited for implantation into regions of the body closer to the body's surface, such as a peripheral artery, since the stent's resilience helps minimize damage or crushing caused by body movement or externally applied forces.

Self-expanding stents may also be used in the coronary arteries and may provide advantages over balloon expandable stents. Balloon expandable stents are expanded with a balloon typically having a constant diameter. Thus, an expanded stent may not conform well to a coronary artery having variations in diameter due to tortuosity or taper. Therefore, there is a potential for gaps between the outer stent surface and the inner surface of the artery wall. These gaps may lead to thrombus formation and recently, there has been concern that this effect is pronounced in drug eluting stents because the drug delays endothelialization of the stent surface, allowing the gaps to remain for a longer period of time. This may be avoided with self-expanding stents that expand until the outer stent surface is constrained by contact with a vessel wall. Therefore, gaps between the stent and the arterial wall are minimized thereby helping to reduce thrombus formation. Companies such as Devax (Irvine, Calif.) and Cardiomind (Sunnyvale, Calif.) are developing self-expanding stents for implantation into the coronary arteries.

While self-expanding stent technology is promising, accurate delivery of the stents to a treatment site can present a challenge. Because self-expanding stent segments tend to rapidly spring open upon deployment, it is often difficult to control their placement. In some cases, the stents may actually eject or jump away from the delivery catheter. Therefore, a delivery system that allows more precise control of stent deployment and placement is desirable.

Current stent delivery technology suffers from some other potential drawbacks which can make delivery of stents challenging. In particular, current stent delivery catheters often employ stents having fixed lengths. The proper selection of fixed length stents requires accurate knowledge of the lesion length being treated. While lesion length may be measured prior to stent deployment using angiography and fluoroscopy, these measurements are often inaccurate. Thus, if an incorrectly sized stent is introduced to a treatment site, it must be removed from the patient along with the delivery catheter and replaced with a different device having the correct stent size. This prolongs the procedure, increases waste and results in a more costly procedure.

Additionally, and especially in the case of peripheral vascular disease, lesions are often long and diffuse. A single long stent may be deployed to treat a single lesion or to span multiple lesions, however this is not optimal since longer stents tend to have higher fracture rates as well as restenosis rates as compared with shorter stents. Therefore, placement of multiple shorter stents in a long lesion may be advantageous instead of deploying a single long length stent.

The use of "custom length" stents as an alternative to fixed length stents has been proposed. One such approach for providing a custom length stent has been to use segmented stents for treatment in which only some of the stents are deployed for treatment. Several exemplary systems are described in several copending, commonly assigned applications which are listed below. In these systems, the stent segments are deployed by selective advancement over the delivery catheter. After delivering an initial group of segments, the catheter may be repositioned to a new treatment site and a further group of segments can then be deployed. These systems enable treatment of multiple lesions with a single device and may contain up to fifty segments.

Another challenge with existing "custom length" stent delivery systems is that to deliver multiple stent segments to multiple lesion sites requires an intricate delivery system that can be somewhat complex to use. Thus, a simpler delivery system that allows length customization is desirable, especially for use in treating long lesions in the peripheral and coronary vasculature.

For the reasons above, as well as others, it would be desirable to provide improved prosthetic stents and delivery catheters that allow better control of stent length and deployment. It would be particularly desirable to provide catheters which enable stent length to be customized using multiple stent segments. It is also desirable to provide a delivery system that is flexible and can track torturous vessels and that has a simple construction and is less costly and easy to use in deploying a selectable number of stent segments to a treatment site. It is further desirable to provide a stent delivery catheter that can control the delivery and placement of self-expanding stents in the peripheral and coronary vascular system.

2. Description of the Background Art

Prior publications describing catheters for delivering multiple segmented stents include: U.S. Publication Nos. 2004/0098081, 2005/0149159, 2004/0093061, 2005/0010276, 2005/0038505, 2004/0186551 and 2003/013266. Prior related unpublished co-pending U.S. patent applications include Ser. No. 11/148,713, filed Jun. 8, 2005, entitled "Devices and Methods for Operating and Controlling Interventional Apparatus"; Ser. No. 11/148,545, filed Jun. 8, 2005, entitled "Apparatus and Methods for Deployment of Multiple Custom-Length Prosthesis"; Ser. No. 11/344,464, filed Jan. 30, 2006, entitled "Apparatus and Methods for Deployment of Custom-Length Prostheses"; Ser. No. 60/784,309, filed Mar. 20, 2006, entitled "Apparatus and Methods for Deployment of Linked Prosthetic Segments"; Ser. No. 11/469,773 filed Sep. 1, 2006, entitled "Custom Length Stent Apparatus"; and Ser. No. 11/462,951, filed Aug. 7, 2006, entitled "Custom Length Stent Apparatus." The full disclosures of each of these patents and applications are incorporated herein by reference.

BRIEF SUMMARY OF THE INVENTION

The invention generally provides for the delivery of self-expanding prostheses with a flexible delivery catheter capable of navigating vessels such as the peripheral and coronary arteries. The delivery catheter permits controlled deployment of a selectable number of prosthetic segments at a treatment site, thus allowing customization of prosthesis length while the delivery catheter is in a body lumen at a treatment site. Customization of prosthesis length in situ permits better matching of the prosthesis length to the lesion length being treated.

The terms "stent" and "stenting" are defined to include any of the array of expandable prostheses and scaffolds which are introduced into a lumen at a target treatment site and expanded in situ thereby exerting a radially outward force against the lumen wall. The prosthesis of the present invention comprises a closed or an open lattice structure and is typically fabricated from an elastic material or self-expanding material, including superelastic materials such as nickel-titanium alloys like Nitinol, or spring temper stainless steels or polymers, and the lattice structures are commonly constrained radially during delivery and upon deployment the constraining structure is removed, allowing the prosthesis to "self-expand" at the target site. The terms "stent," "prosthesis," "prosthetic segment" and "stent segment" refer broadly to all radially expansible stents, grafts, and other scaffold-like structures which are intended for deployment within a body lumen.

In a first aspect of the present invention, a catheter for delivering a prosthesis to a treatment site in a body lumen comprises a pusher tube having a proximal end and a distal end and a sheath that is slidably disposed over the pusher tube. The catheter includes one or more self-expanding tubular prostheses that are carried within the sheath. The sheath constrains the one or more prostheses in a radially contracted configuration and the one or more prostheses are independently releasable from the sheath as the sheath is retracted relative to the pusher tube. The pusher tube is adapted to prevent proximal motion of the one or more self-expanding prostheses as the sheath is retracted. The one or more prostheses resiliently expand upon release from the sheath. The catheter also includes a radially expandable control member that is positionable within the one or more prostheses and that has an expanded shape which engages an inner surface of at least one of the one or more prostheses to exert an outward force against the prosthesis. This urges the prosthesis outwardly against an interior surface of the sheath. The control member is also axially movable with the sheath so that it slides relative to the prostheses that are in engagement therewith as the sheath is retracted relative to the pusher tube. The catheter may further comprise a handle near the proximal end of the pusher tube. The handle often has a control mechanism adapted to actuate the sheath and the radially expandable control member during deployment of the self-expanding prostheses. The pusher tube may be proximal to the self-expanding prostheses and may be adapted to engage a prosthesis in the sheath for retrieval thereof, thereby preventing the prosthesis from being deployed. The catheter may also comprise an elongate flexible member that is disposed at least partially under the pusher tube. Sometimes the elongate flexible member has a lumen therethrough that is adapted to receive a guidewire.

In another aspect of the present invention, a catheter for delivering a prosthesis to a treatment site in a body lumen comprises a pusher tube having a proximal end and a distal end, and a sheath with a distal tip. The sheath is slidably disposed over the pusher tube. The catheter also has one or more self-expanding tubular prostheses carried within the sheath. The sheath constrains the prostheses in a radially contracted configuration and the prostheses are independently releasable from the sheath as the sheath is retracted relative to the pusher tube. The prostheses resiliently expand upon release from the sheath. A radially expandable control member is positioned within the prostheses and has an expanded shape which engages an inner surface of at least one of the prostheses to exert an outward force against the prosthesis so as to urge it outwardly against the sheath. The control member is axially movable with the sheath so as to slide relative to the prosthesis in engagement therewith as the sheath is retracted relative to the pusher tube. The distal tip of the sheath is also interactive with the control member to enable a prosthesis to be trapped therebetween to inhibit the prosthesis from jumping distally upon expansion. The catheter may also have a handle near the proximal end of the pusher tube. The handle often has a control mechanism that is adapted to actuate the sheath and the radially expandable control member during deployment of the self-expanding prostheses. The pusher tube is adapted to prevent proximal motion of the one or more self-expanding prostheses as the sheath is retracted and may be proximal to the self-expanding prostheses. The pusher may also be adapted to engage a prosthesis in the sheath for retrieval thereof, thereby preventing the prosthesis from being deployed. The catheter may also comprise an elongate flexible member that is disposed at least partially under the pusher tube. Sometimes the elongate flexible member has a lumen therethrough that is adapted to receive a guidewire.

In another aspect of the present invention, a method of delivering a prosthesis to a treatment site in a body lumen comprises positioning a delivery catheter at the treatment site. The delivery catheter may have one or more self-expanding tubular prostheses thereon and the prostheses are usually covered by a sheath. Retracting the sheath exposes a prosthesis which resiliently expands radially into contact with a wall of the body lumen. A control member slidably coupled to the delivery catheter is radially expanded. The control member engages an interior surface of the prosthesis as the sheath is retracted. The control member is retracted in conjunction with the sheath and exerts an outward force against the prosthesis to urge the prosthesis outwardly against the sheath to maintain the axial position of the prosthesis relative to the delivery catheter as the prosthesis is released from the sheath.

The self-expanding tubular prosthesis is then released from the delivery catheter into the body lumen.

Often, releasing the prosthesis comprises collapsing the radially expandable control member so that the control member disengages from the inner surface of the prosthesis. Sometimes, releasing the prosthesis comprises deflating a balloon. The method may further comprise retracting the control member axially in conjunction with the sheath so as to slide relative to the prosthesis in engagement therewith. Engaging the prosthesis may comprise inflating a balloon. Sometimes, another prosthesis is retained in the sheath after the prosthesis is released.

Often, the radially expandable control member is metal although it may be a polymer and comprises a plurality of elongate struts disposed distal to the pusher tube. The struts may be resilient and can bend outwardly under compression. Often the expandable member is a basket having a plurality of flexible strands. Some of the strands may be axially oriented and bend outwardly under compression. Often the strands are metal, although they may be a polymer. Sometimes the expandable member comprises a polymer and may be a balloon. The radially expandable control member may engage at least two self-expanding prostheses simultaneously.

The sheath may be adapted to be retracted while the pusher tube remains fixed relative to the handle so as to expose at least one of the self-expanding tubular prostheses for deployment. Sometimes the sheath has a distal tip that is interactive with the control member to enable a self-expanding prosthesis to be trapped therebetween to inhibit the prosthesis from jumping distally upon expansion. The distal tip may be flared and often is expandable as the prosthesis expands. Sometimes the distal tip has a plurality of axial slits.

A distal end of the sheath may radially expand or flare outwardly as the self-expanding prostheses expand. Often an outward force exerted by the control member or the self-expanding prostheses expands the distal sheath end. When the distal end of the sheath is axially split into sections, the sections deflect outwardly as the prostheses expand. Usually, the distal end of the sheath resiliently returns to a non-expanded shape following release of the desired number of prostheses or when the control member is retracted back into the sheath.

In yet another aspect of the present invention, a self-expanding tubular prosthesis comprises a plurality of self-expanding tubular rings having a plurality of axial struts and a plurality of connectors coupling adjacent struts together. The axial struts and the connectors often form a zig-zag pattern. A bridge member couples adjacent tubular rings together and the prosthesis also has an interlocking tab coupled to a tubular ring on one end of the tubular prosthesis with a flexible connector. The interlocking tab is adapted to interlock with an adjacent prosthesis prior to expansion of the prosthesis and the flexible connector also allows radial flexing of the interlocking tab relative to the tubular prosthesis.

The plurality of connectors are often substantially U-shaped and the bridge member is often sigmoidal shaped. Usually, the bridge member is coupled to at least one of the plurality of connectors. Sometimes, a first bridge member on a proximal end of the prosthesis has a first slope and a second bridge member on a distal end of the prosthesis has a second slope opposite of the first slope. The interlocking tab may comprise an enlarged head region and a narrower neck region. The enlarged head region often comprises an arcuate strut that defines a narrow inlet portion and a wider receiving portion with the receiving portion adapted to receive and interlock with an interlocking tab on an adjacent prosthesis. The receiving portion also may have a surface that is substantially transverse to a longitudinal axis of the prosthesis. This surface allows the prosthesis to be pushed in a direction that is substantially parallel to the longitudinal axis. Sometimes, the interlocking tab may have a strut which defines an aperture for holding a radiopaque marker.

The catheter may have a plurality of self-expanding prostheses. The prostheses often have a length in the range of about 2 mm to about 50 mm. Sometimes each of the prostheses may have the same length or at least one of the prostheses has a length different than at least another of the prostheses. Often the prostheses have ends in engagement with one another prior to deployment. Sometimes the prostheses are axially connected to each other when in the sheath and they may disconnect from one another upon expansion. The self-expanding tubular prostheses often carry a therapeutic agent adapted to being released therefrom and sometimes the agent is an anti-restenosis agent.

These and other embodiments are described in further detail in the following description related to the appended drawing figures.

BRIEF DESCRIPTION OF THE DRAWINGS

FIGS. 2A-2F show selection and deployment of prostheses in accordance with an exemplary embodiment.

FIGS. 3A-3D show selection and deployment of prostheses in accordance with another exemplary embodiment.

FIGS. 5A-5B show an embodiment of a stent delivery catheter having a flexible distal sheath tip.

FIG. 6A illustrates a top view of another embodiment of a prosthesis after it has been unrolled and flattened.

FIG. 6B illustrates interconnection of prosthesis ends.

FIG. 7A shows a top view of yet another embodiment of a prosthesis after it has been unrolled and flattened.

FIG. 7B shows interconnection of the prosthesis illustrated in FIG. 7A with another prosthesis.

FIG. 8A shows a top view of still another embodiment of a prosthesis after it has been unrolled and flattened.

FIG. 8B shows the end of the prosthesis illustrated in FIG. 8A interconnecting with the end of an adjacent prosthesis.

DETAILED DESCRIPTION OF THE INVENTION

Figure 1A:
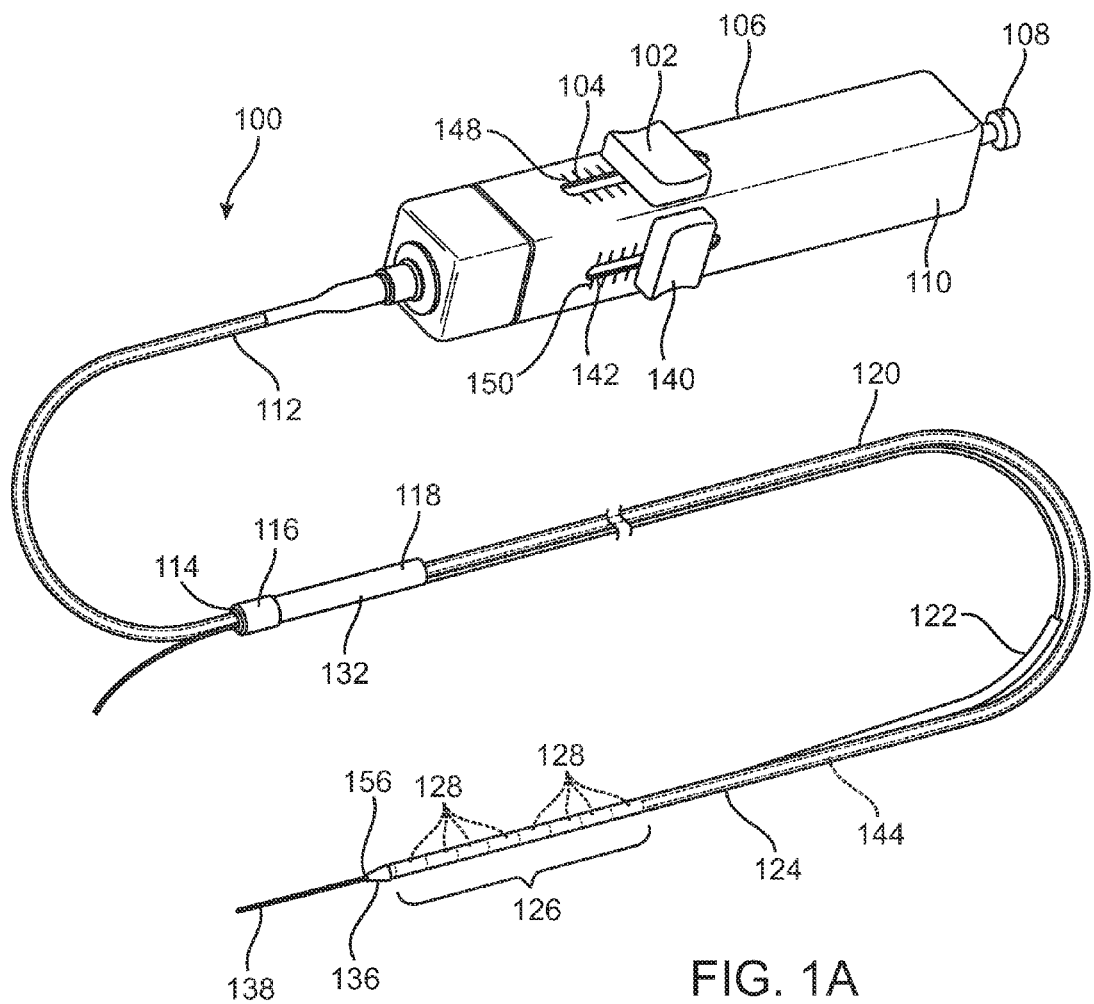
FIG. 1A is a perspective view of a stent delivery catheter in accordance with one embodiment of the present invention.
Figure 1B:
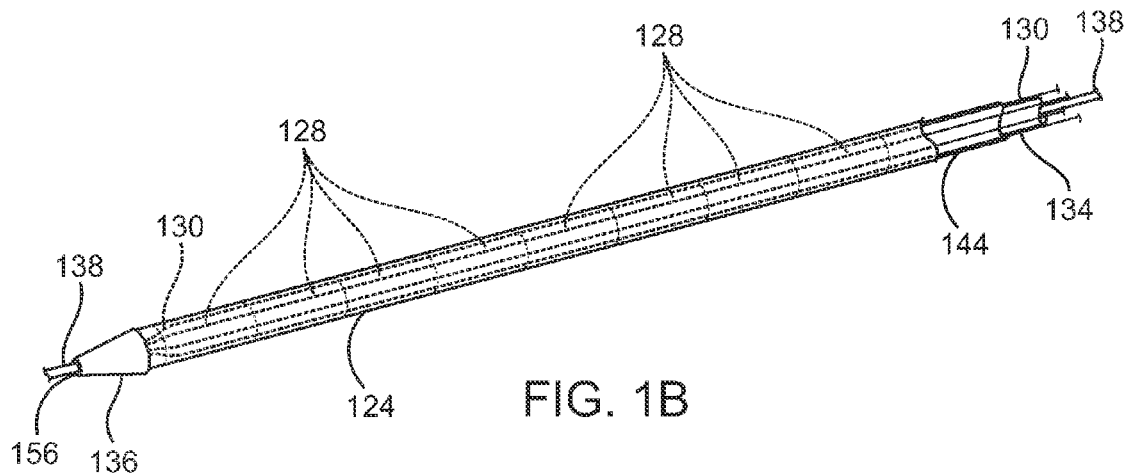
FIG. 1B is a perspective view of the distal end of the stent delivery catheter shown in FIG. 1A.

Referring now to FIG. 1A, a stent delivery catheter 100 comprises a catheter shaft 120 which includes a sheath 124 slidably disposed over a pusher tube 144 which is in turn slidably disposed over an inner shaft 134 (seen in FIG. 1B). A prosthesis 126 is carried near the distal end of the catheter shaft 120 and is covered by sheath 124. Pusher tube 144 serves as a backstop and prevents prosthesis 126 from moving proximally when sheath 124 is retracted. A radially expandable control member 130, is slidably disposed over inner shaft 134 and is positionable within prosthesis 126, under sheath 124. A tapered nosecone 136 having a distal exit port 156, composed of a soft elastomeric material to minimize trauma to the vessel during advancement of the delivery catheter 100, is attached to the inner shaft 134 distally of the radially expandable control member 130. Prosthesis 126 preferably comprises a plurality of self-expanding prostheses 128 mounted under sheath 124 and disposed over the radially expandable control member 130. Sheath 124 covers the self-expanding prosthetic segments 128 and constrains them in a radially contracted configuration until the delivery catheter 100 has been properly positioned at a treatment site. A radiopaque marker 152 (FIG. 1C) near the distal end of sheath 124 helps the operator visualize the delivery catheter under fluoroscopy during a stent procedure. Radiopaque marker 152 also helps the operator to view the distance the sheath has been retracted relative to the nosecone 136. This will be discussed in greater detail below. An optional expandable distal portion 154 of sheath 124 may be used to help trap prostheses 128 between the flexible sheath tip 154 and the expandable control member 130 during deployment thereby controlling axial movement of the prostheses 128, which is discussed in greater detail below.

Figure 1C:
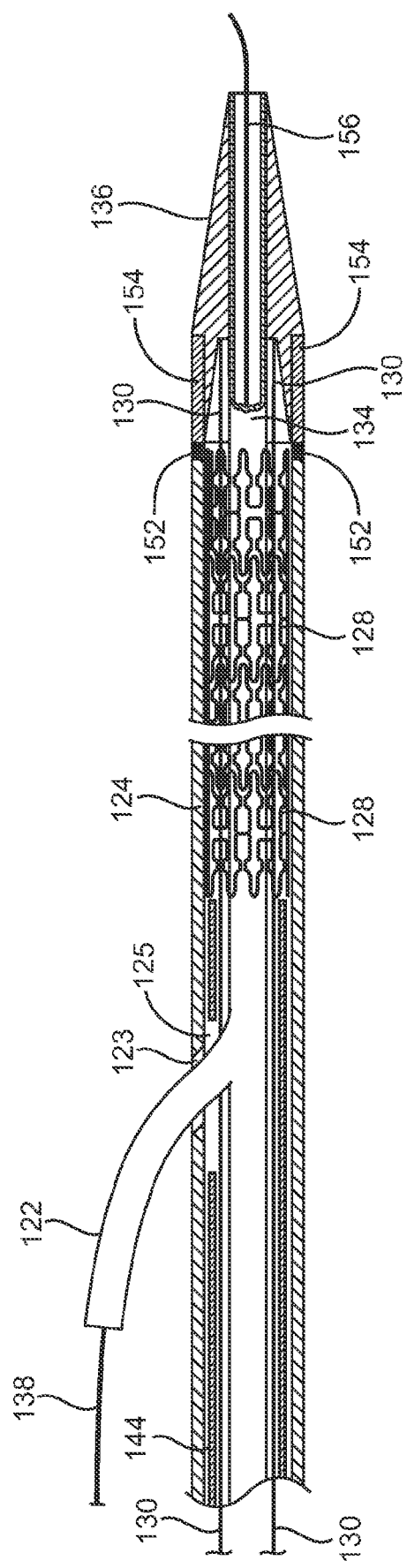
FIG. 1C shows a cross-section of the distal end of the stent delivery catheter shown in FIG. 1A.

In the present embodiment shown in FIGS. 1A-1C, an optional guidewire tube 122 is slidably positioned through both sheath 124 and inner shaft 134 and proximal to the prosthesis 126. A guidewire 138 is positioned slidably through guidewire tube 122 and nosecone 136 and exits a distal exit port 156, extending distally thereof. Axial slots 123 and 125 in outer sheath 124 and pusher tube 144, respectively, allow outer sheath 124 to be retracted smoothly over guidewire tube 122 without binding due to interference between the moving portions. The delivery catheter may also be fabricated without a guidewire tube 122 and this preferred embodiment is discussed later. FIG. 1A illustrates the stent delivery catheter 100 and FIG. 1B highlights the distal end of delivery catheter 100. FIG. 1C is a cross-sectional view of the distal end of delivery catheter 100.

As shown in FIG. 1A, a handle 106 is attached to a proximal end 112 of the outer sheath 124. The handle 106 performs several functions, including retracting and advancing outer sheath 124 and radially expandable control member 130 thereby exposing prosthetic segments 128 and allowing the prosthetic segments 128 to self-expand and be deployed.

Handle 106 includes a housing 110 which encloses the internal components of the handle 106. Handle 106 allows a physician operator to advance or retract outer sheath 124 and radially expandable control member 130. The amount of retraction of sheath 124 determines the number of individual prostheses 128 to be deployed thereby establishing the overall length of prosthesis 126, while ensuring accurate delivery of the individual prostheses 128. The inner shaft 134 is preferably fixed to the handle housing 110, although in some embodiments it may also be operatively coupled with handle 106 to be axially moveable. Both outer sheath 124 and radially expandable control member 130 are coupled to slide mechanisms 102 and 140, respectively. Slide mechanisms 102 and 140 allow both the outer sheath 124 and radially expandable control member 130 to be retracted and advanced relative to handle 106. Optionally, a single slide mechanism could be used to control motion of the outer sheath 124 and radially expandable control member 130.

Slide mechanism 102 is coupled with outer sheath 124 and translates along calibrated slot 104. Slide mechanism 102 is adapted to retract the outer sheath 124 a selected distance so that the self-expanding tubular prostheses 128 may be exposed for delivery. The radially expandable control member 130 is operatively coupled with outer sheath 124 and therefore slide mechanism 102 also retracts radially expandable control member 130 with sheath 124. A small offset is built into the slide mechanism 102 so that outer sheath 124 may be retracted a short distance prior to engaging and retracting expandable control member 130. This offset is approximately 2 mm to 50 mm and allows the radially expandable control member 130 to expand along with the prosthesis 128 once the constraint provided by outer sheath 124 has been removed. As sheath 124 is retracted, the distal most section of prosthesis 128 begins to expand along with the radially expandable control member 130. As slide 102 is further retracted, outer sheath 124 engages and cooperatively retracts with control member 130. Additional details on the operation of sheath 124 and radially expandable control member 130 are described below. The slide mechanism 102 includes visual markers 148 so that an operator can easily determine the length or number of prostheses that have been exposed. In preferred embodiments, slide mechanism 102 may have detents or a ratchet that provides audible or tactile feedback to the operator to facilitate operation of the stent delivery catheter 100 without requiring direct visualization during operation.

Handle 106 also comprises a second control mechanism 140 that translates along calibrated slot 142. Slide mechanism 140 is coupled with the radially expandable control member 130 and is adapted to retract or advance the control member 130 independently of outer sheath 124. For example, after the number of prosthetic segments 128 has been selected, exposed and deployed as described above, radially expandable control member 130 may be removed from within the deployed stent segments 128 and this may be accomplished by retracting slider 140 so as to collapse the radially expandable control member 130 back into outer sheath 124. In alternative embodiments, sheath 124 may be advanced over the radially expandable control member 130 thereby collapsing it. Slide mechanism 140 also includes visual markers 150 that help the physician determine the position of the control member relative to sheath 124. Additionally, the slide mechanism 140 may comprise detents or a ratchet that further assists physician operation by providing audible or tactile feedback. Further details on operation of the radially expandable control member 130 and the outer sheath 124 are discussed below.

Handle 106 also permits optional connection of an external fluid source via adapter 108 attached to the proximal end of handle 106. Fluid may then be injected at the proximal handle end and infused along a lumen in inner shaft 134 into a patient via infusion ports (not shown) near the distal end of the delivery catheter 100 or via the distal exit port 156. Adaptor 108, preferably a Luer connector, is configured to be fluidly coupled with a fluid source such as a syringe or intravenous bag. In alternative embodiments adaptor 108 may be fluidly connected to an inflation lumen in inner shaft 134 which is connected to an inflatable control member at the distal end of the catheter. The inflatable control member may be a balloon. An inflation device which may be any commercially available balloon inflation device such as those sold under the trade name "Indeflator™," manufactured by Abbott (formerly Guidant Corporation of Santa Clara, Calif.) may then be connected to adaptor 108 to deliver an inflation fluid to the control member.

Additional details on materials and construction of other suitable handles and control mechanisms are described in co-pending U.S. patent application Ser. No. 11/148,713, filed Jun. 8, 2005, entitled "Devices and Methods for Operating and Controlling Interventional Apparatus," and co-pending United States Publication No. 2005/0149159, entitled "Devices and Methods for Controlling and Indicating the Length of an Interventional Element," and application Ser. No. 11/614,271, filed Dec. 21, 2006, formerly 021629-003800US), entitled "Custom Length Stent Apparatus," the full disclosures of which are incorporated herein by reference.

Both outer sheath 124 and guidewire 138 each may extend through an optional slider assembly 132 slidably disposed on the catheter body 120 at a point between its handle 106 and prostheses 128. Optionally, in other embodiments, sheath 124 may extend through slider 132 with the guidewire 138 running axially along the outside of slider 132. The slider assembly 132 is adapted for insertion into and sealing with a hemostasis valve, such as on an introducer sheath or guiding catheter, while still allowing relative movement of the outer sheath 124 relative to the slider assembly 132. The slider assembly 132 includes a slider tube 118, a slider body 116, and a slider cap 114.

Outer sheath 124 may be composed of any of a variety of biocompatible materials, such as but not limited to a polymer like PTFE, FEP, polyimide, Nylon, Pebax, or metals including Nitinol or stainless steel. Outer sheath 124 may also be reinforced with a metallic or polymeric braid to resist radial expansion of radially expandable control member 130 and self-expanding prostheses 128. Similar materials may also be used for the inner shaft 134 and the pusher tube 144. Additional aspects of the luminal prosthesis delivery system are described in U.S. patent application Ser. No. 10/306,813, filed Nov. 27, 2002; U.S. patent application Ser. No. 10/637,713, filed Aug. 8, 2003; U.S. patent application Ser. No. 10/738,666, filed Dec. 16, 2003; and U.S. patent application Ser. No. 11/104,305, filed Apr. 11, 2005; the full disclosures of which are hereby incorporated by reference.

Although not required, in preferred embodiments, outer sheath 124 may further comprise an optional flexible distal tip which interacts with the self-expanding prostheses 128 during deployment. FIGS. 5A-5B illustrate one embodiment of the flexible distal sheath tip and radially expandable control member. In FIG. 5A the distal tip of outer sheath 502 comprises a plurality of axial slits defining a plurality of deflectable sections or petals 506. Petals 506 may be fabricated from materials such as but not limited to, PEEK, polyimide, PTFE, polyethylene or metals such as Nitinol or stainless steel. The tips of sections 506 are disposed within an aperture on the proximal end of nosecone 508 so that the tips do not flare out until outer sheath 502 is retracted. In alternative embodiments, the distal tip of outer sheath 502 may also butt up against nosecone 508. The outer sheath 502 also may comprise an optional reinforced region 504 near the distal sheath end. This reinforced region 504 may be formed by bonding a polymeric sleeve to the outer sheath 502 to help attach petals 506 thereto. FIG. 5B shows how the distal tip 506 of outer sheath 502 expands during deployment of the prostheses. In FIG. 5B, outer sheath 502 is retracted proximally, pulling the outer sheath tip 502 away from nosecone 508 and also exposing radially expandable control member 510. Radially expandable control member 510 comprises a plurality of resilient axial struts 511 which self-expand outwardly to form a wire-like basket. The struts 511 are preferably formed from a tube having a plurality of axial slits. As struts 511 expand, the distal tip 506 of outer sheath 502 also flexes outwardly forming a plurality of sections 506. Four to eight petals may be used, although preferably six petals are used. The prostheses (not shown) are therefore trapped between the petals 506 of the flexible sheath tip and the radially expandable control member 510 which controls axial movement of the prostheses during deployment. Other embodiments of the radially expandable control member 510 are discussed below.

Figure 1D:
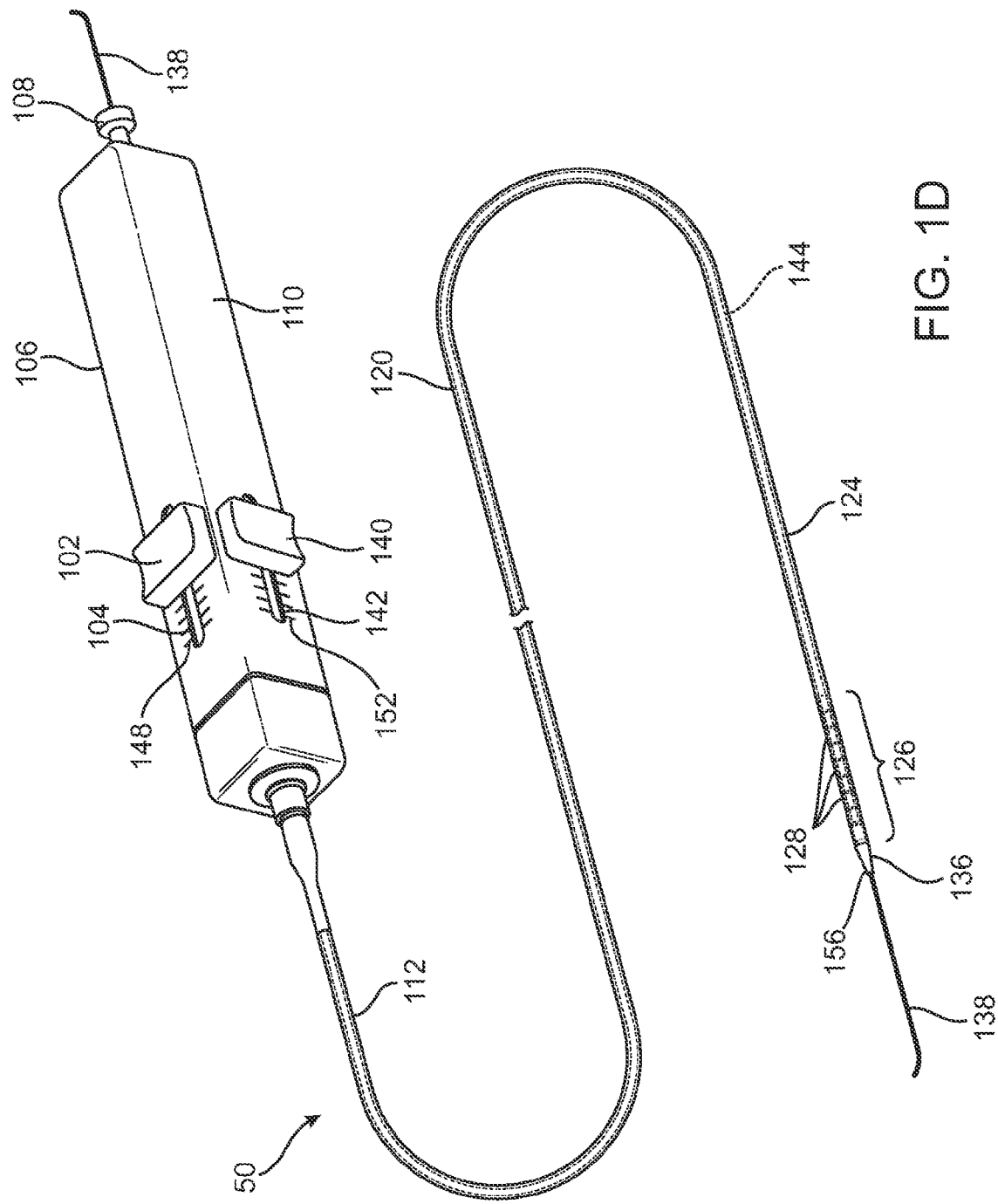
FIG. 1D shows a perspective view of an over the wire stent delivery catheter in accordance with another embodiment of the present invention.
Figure 1E:
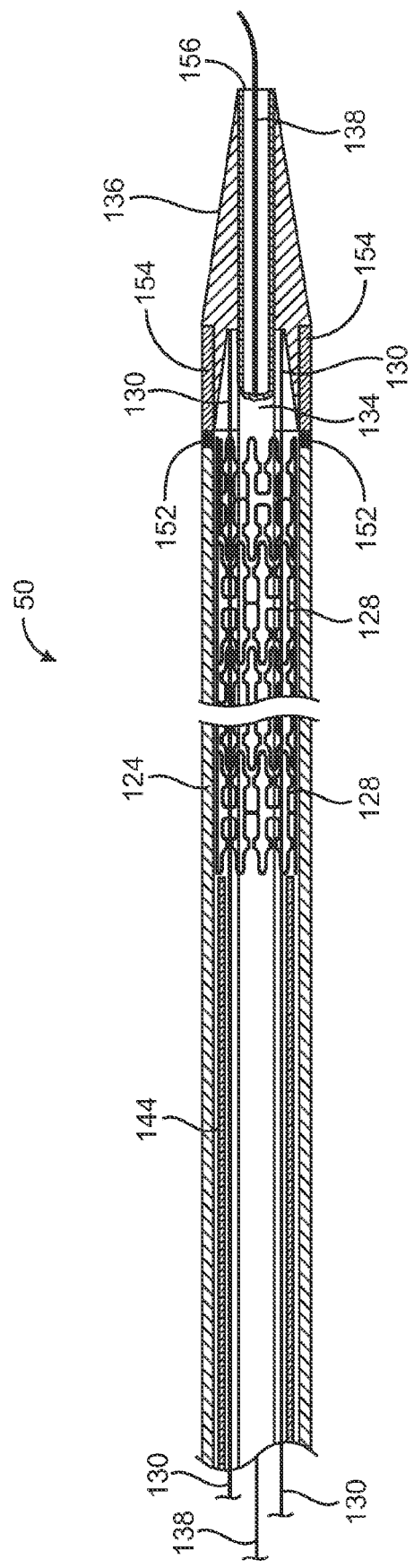
FIG. 1E illustrates a cross-sectional view of the embodiment in FIG. 1D.

FIG. 1D illustrates an over-the-wire embodiment of a prosthesis delivery catheter 50. This preferred embodiment differs from the previous embodiment in that it does not have a guidewire tube exiting near the distal end of the delivery catheter. Instead, an optional inner shaft 134 with a central lumen traverses the length of the delivery catheter allowing catheter 50 to be advanced over a guidewire. Other structural and functional aspects of delivery catheter 50 generally take the same form as delivery catheter 100 which was previously discussed. Delivery catheter 50 may also include a slider assembly (not illustrated) such as slider 132 previously described above. FIG. 1D shows a perspective view of the over-the-wire embodiment and FIG. 1E shows a cross-sectional view of the distal end of catheter 50.

In the embodiments of FIGS. 1A-1C and FIGS. 1D-1E, prosthesis 126 is composed of one or more prostheses segments 128. Prosthetic stent segments 128 are disposed over the inner shaft 134 and under sheath 124. Each stent segment is about 3-50 mm in length, more typically about 10-30 mm in length and preferably being about 15-25 mm in length. Segment length often may be 20 mm to 40 mm long in superficial femoral artery or below the knee implantations while segment length often is 4 mm to 8 mm in coronary use. Usually 1-20, more typically 2-15 and preferably 5-10 stent segments 128 are positioned axially over the inner shaft 134. Stent segments 128 are preferably positioned in direct contact with an adjacent stent segment 128 so that segment ends are in engagement and interlocked with one another. Furthermore, the stent segments 128 may be deployed individually or in groups of two or more at a single treatment site within the vessel lumen.

Figure 4A:
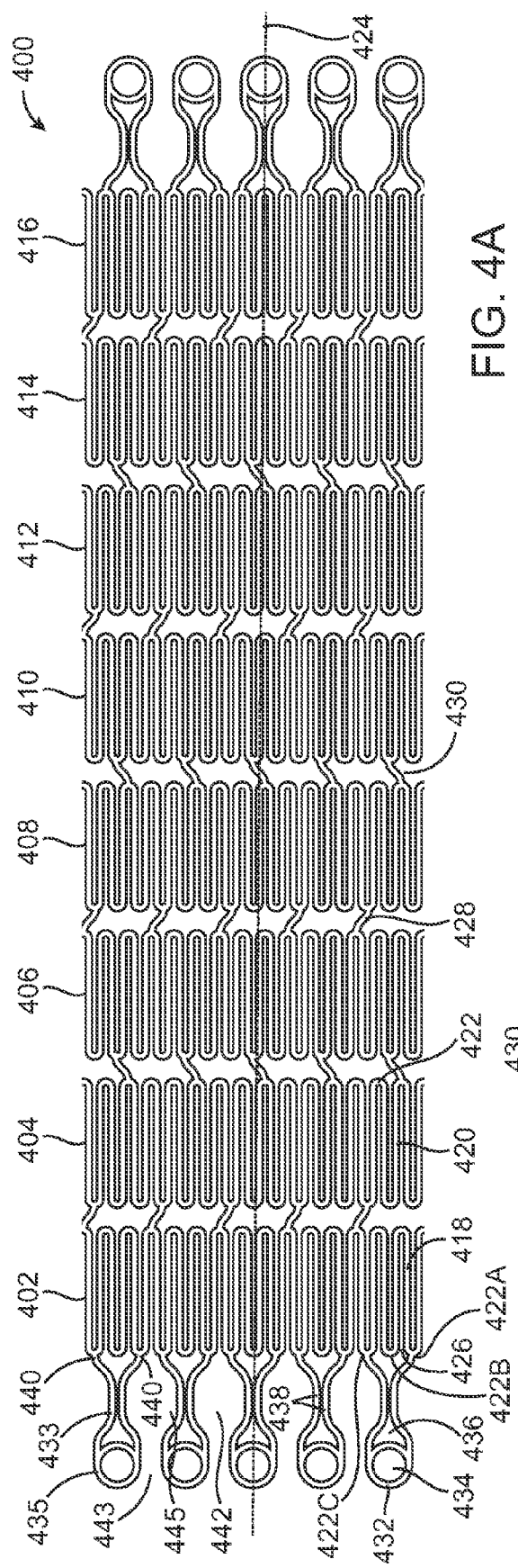
FIG. 4A shows a top view of a prosthesis after it has been unrolled and flattened.

In preferred embodiments the adjacent ends have axially extending members that interleave with one another. In a preferred embodiment seen in FIG. 4A, the geometry of prosthesis 400 is illustrated in an unexpanded configuration, unrolled and flattened out for clarity. In FIG. 4A, prosthesis 400 comprises eight parallel columns 402, 404, 406, 408, 410, 412, 414 and 416 of open cells 426, spaced apart by a gap 430 and formed around a central axis 424 so that prosthesis 400 has a tubular or cylindrical shape. Each column 402, 404, 406, 408, 410, 412, 414 and 416 is formed from an undulating, zig-zag or wave pattern 418. The wave pattern 418 is comprised of substantially axial struts 420 joined together by a U-shaped connector 422. The struts 420 are generally parallel to the central axis 424.

In this preferred embodiment, each wave pattern 418 repeats itself fourteen times in each of the eight parallel columns 402, 404, 406, 408, 410, 412, 414, 416 of open cells 426, although this number is not intended to be limiting. The number of rows of cells may be increased to provide increased scaffolding of the lumen wall or the number of rows may be decreased to minimize the amount of metal in the prosthesis which contacts the lumen wall. The wave pattern 418 in each column is out-of-phase with the adjacent column, therefore the peak of one sinusoidal-like wave pattern is adjacent to the trough of a sinusoidal-like wave 418 pattern in an adjacent column. In addition, the parallel columns 402, 404, 406, 408, 410, 412, 414, 416 of open cells 426 are joined together by a sigmoidal shaped connector 428 which joins the ends of U-shaped connector 422 together.

The sigmoidal connector 428 generally attaches to the apex of the U-shaped connector 422. Also, the sigmoidal shaped connector 428 attaches generally to every third U-shaped connector 422, in each column 402, 404, 406, 408, 410, 412, 414, 416, thus there are five sigmoidal shaped connectors 428 between each column 402, 404, 406, 408, 410, 412, 414 and 416 of open cells 426. Additionally, the slope of the sigmoidal shaped connectors 428 alternate between columns 402, 404, 406, 408, 410, 412, 414 and 416 of open cells 426. For example, the sigmoidal shaped connector 428 between column 402 and 404 is attached to the U-shaped connector 422 in column 402 at a point generally at the center of the valley of the U-shaped connector 422 and substantially parallel to the axial struts 420. The sigmoidal connector 428 slopes downward toward the adjacent U-shaped connector 422 in the adjacent column 404 and attaches to the adjacent U-shaped connector 422 at a point generally at the center of the peak of the U-shaped connector 422 and substantially parallel to the axial struts 420. The sigmoidal shaped connector 422 between columns 404 and 406 similarly joins U-shaped connectors 422, except this time slopes upward. This pattern alternates across the prosthesis 400 so that there are four sets of sigmoidal shaped connectors 428 sloping downward and three sets of sigmoidal shaped connectors 428 that slope upward. Therefore because the columns 402, 404, 406, 408, 410, 412, 414, 416 of wave patterns 418 are out-of-phase, the U-shaped connectors 422 join cells 426 in a staggered fashion.

Figure 4B:
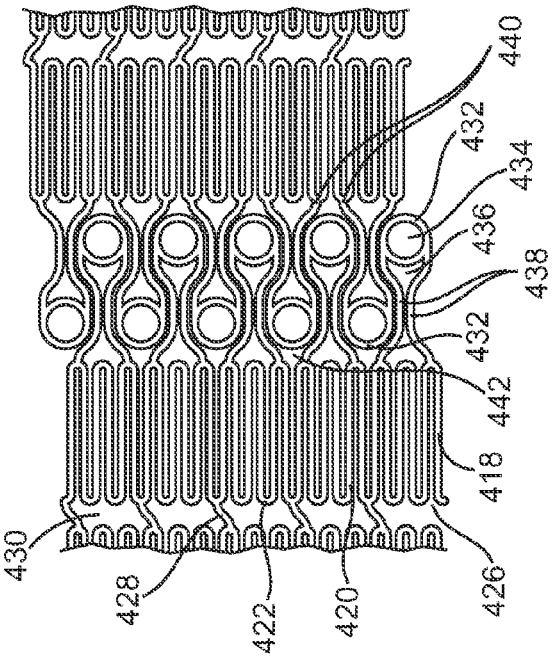
FIG. 4B shows interconnection of prostheses ends.

Both ends of prosthesis 400 also comprise locking tabs 432 having a narrow neck portion 433 and a wider head portion 435 defined by curved struts 438. Each locking tab 432 is joined to the body of the prosthesis 400 by curved struts 438 which join alternating U-shaped connectors 422 at their apex 440 and form a first subcell 436 and a second subcell 434 which serves as an enlarged flange region of the locking tab 432. Curved struts 438 join two U-shaped connectors 422A, 422C, which are separated by one intervening U-shaped connector 422B. In some embodiments, the second subcell 434 may be fitted with an optional radiopaque marker to enhance visibility of the prosthesis under a fluoroscope. A space 442 is disposed between locking tabs 432, defined by a narrow inlet portion 443 and a wider receiver portion 445 adapted to receive the locking tab 432 from an adjacent prosthesis 400. Locking tabs 432 on the opposite end of prosthesis 400 are circumferentially offset with respect to the first end so that adjacent prostheses may interleave and engage with one another. FIG. 4B illustrates how the ends of prostheses 400 with locking tabs 432 engage one another.

Figure 4C:
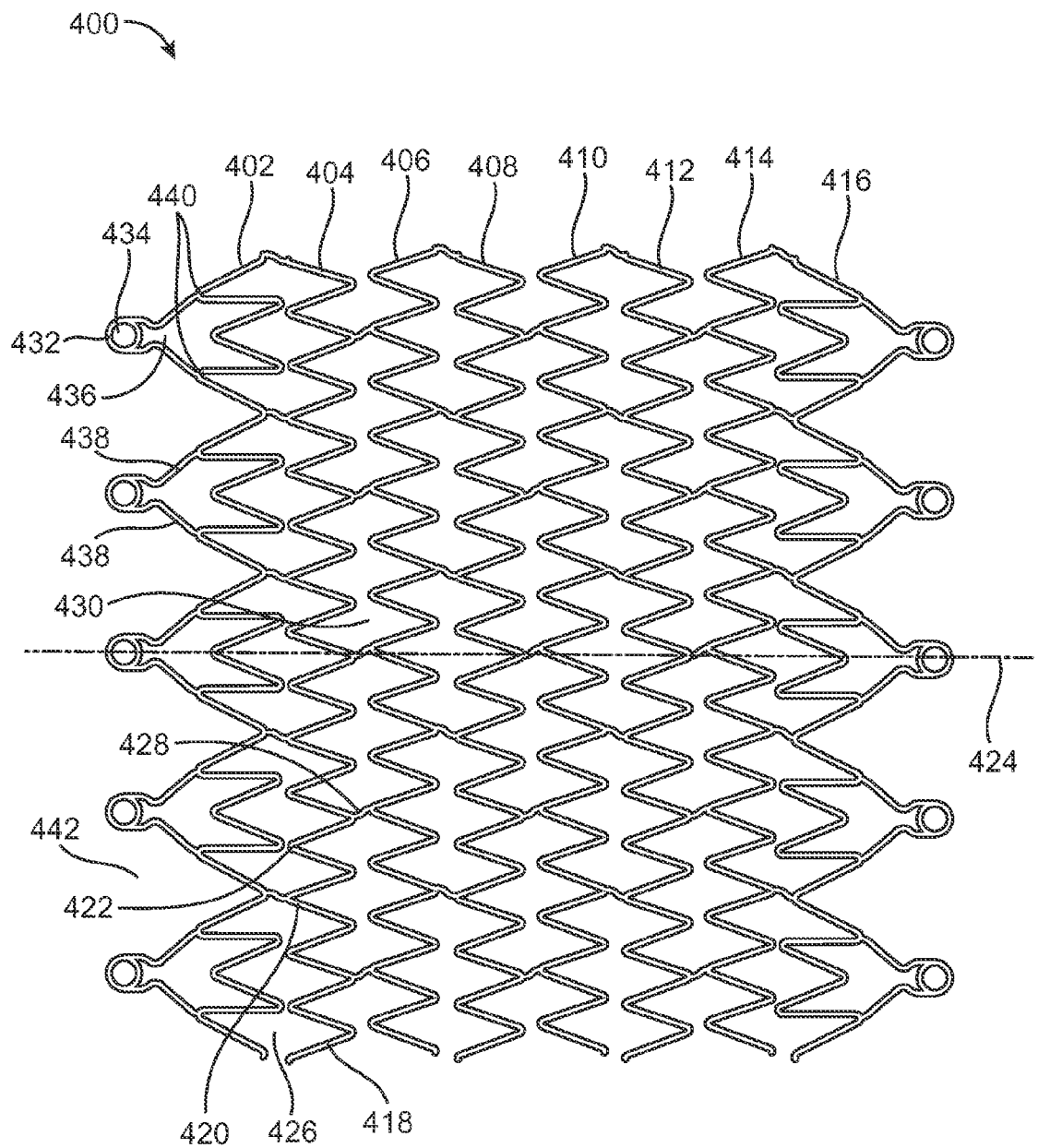
FIG. 4C shows a top view of the prosthesis shown in FIG. 4A after it has self-expanded.

FIG. 4C illustrates prosthesis 400 of FIGS. 4A-4B in the expanded configuration, unrolled and flattened. In the expanded configuration, U-shaped connectors 422 deflect outwardly, expanding cells 426. Struts 420, while still substantially straight, are no longer horizontal and thus the period of the sinusoidal-like wave pattern forming each cell 426 has increased and become more angular to form more of a zig-zag, thereby increasing the diameter of the prosthesis. Cells 426 which originally appear as a series of horizontally oriented ovals, now appear as a series of triangles or diamonds. The radial expansion of prosthesis 400 also results in some shortening of the prosthesis in the axial direction. Sigmoidal connectors 428 maintain the spacing 430 between columns of cells 418. Additionally, the space 442 between locking tabs 432 has also been expanded circumferentially, thereby releasing the locking tabs 432 on the adjacent prosthesis 400.

FIG. 6A illustrates another preferred embodiment of a prosthesis 600 in the unexpanded configuration and unrolled and flattened out for clarity. This embodiment is similar to the previous embodiment illustrated in FIGS. 4A-4C, with the major differences being the number of columns of open cells, a hinge connecting the axially extending interlocking members to the ends of the prosthesis and a more arcuate connector between columns and radiopaque markers in the interlocking members. In FIG. 6A, prostheses 600 comprises ten parallel columns 602a, 602b, 602c, 602d, 602e, 602f, 602g, 602h, 602i, 602j of open cells 626, spaced apart by a gap 630 and formed around a central axis 624 so that prosthesis 600 has a tubular or cylindrical shape. The number or width of columns may be adjusted to increase or decrease the overall length of prosthesis 600. Adjusting the width of a column also controls the radial strength of the stent. Thus, in FIG. 6A, columns 602a and 602j are more easily radially compressible than the other columns because the axial struts 620 are slightly longer than the other columns. Adjusting column width therefore allows a stent to be created with variable radial strength along its longitudinal axis. Each column 602a, 602b, 602c, 602d, 602e, 602f, 602g, 602h, 602i, 602j is formed from an undulating, sinusoidal-like zig-zag or wave pattern 618. The wave pattern 618 is comprised substantially of axial struts 620 joined together by a U-shaped connector 622. The struts 620 are generally parallel to the central axis 624.

In this preferred embodiment, each wave pattern 618 repeats itself eighteen times in each of the ten parallel columns 602a, 602b, 602c, 602d, 602e, 602f, 602g, 602h, 602i, 602j of open cells 626, although this number is not meant to be limiting. The number of rows of cells may be increased to provide increased scaffolding of the lumen wall or the number of rows may be decreased to minimize the amount of metal in the prostheses which contacts the lumen wall. The wave pattern 618 in each column is out-of-phase with the adjacent column, therefore the peak of one sinusoidal-like wave patterns is adjacent to the trough of a sinusoidal-like wave 618 pattern in an adjacent column. In addition, the parallel columns 602a, 602b, 602c, 602d, 602e, 602f, 602g, 602h, 602i, 602j of open cells 626 are joined together by a sigmoidal shaped connector 628 which joins the ends of U-shaped connector 622.

The sigmoidal shaped connector 628 attaches generally to every third U-shaped connector 622, in each column 602a, 602b, 602c, 602d, 602e, 602f, 602g, 602h, 602i, 602j thus there are six sigmoidal shaped connectors 628 between each column 602a, 602b, 602c, 602d, 602e, 602f, 602g, 602h, 602i, 602j of open cells 626. Additionally, the slope of the sigmoidal shaped connectors 628 alternate between columns 602a, 602b, 602c, 602d, 602e, 602f, 602g, 602h, 602i, 602j of open cells 626. For example, the sigmoidal shaped connector 628 between column 602a and 602b is connected to U-shaped connector 622 substantially parallel to axial struts 620 and at a point in column 602a that is lower than the U-shaped connector 622 in adjacent column 602b. The sigmoidal connector is connected to adjacent U-shaped connector 622 in column 602b substantially parallel to axial struts 620, but at a point higher than in column 602a. Therefore, sigmoidal connector generally slopes upward. The sigmoidal connector 622 slopes downward between the next set of columns 602b and 602c, and this pattern alternates across prosthesis 600 so that there are a total of five sets of sigmoidal connectors 622 that slope upward and four sets that slope downward. Additionally, the sigmoidal connectors 622 are staggered between columns 602a, 602b, 602c, 602d, 602e, 602f, 602g, 602h, 602i, 602j. Sigmoidal connectors 622 that slope upward are all along the same row, while sigmoidal connectors 622 that slope downward are in a different row and thus offset from those that slope upward, thereby creating a staggered pattern.

Both ends of prosthesis 600 also have locking tabs 632 having a narrow neck portion 633 and a wider head portion 635 defined by curved struts 638. Locking tabs 632 are staggered so that adjacent prostheses 600 may interlock with one another. Each locking tab 632 is joined to the body of prosthesis 600 by a pair of zig-zag shaped connectors 639 which are coupled to every other U-shaped connector 622 at a point 640 which is slightly offset from the apex of the U-shaped connector 622. Connector 639 also permits the locking tabs 632 to radially deflect relative to the prosthesis 600. This point alternates from slightly above the apex to slightly below the apex between connection points. The curved struts 638 also form a first subcell 636 and a second subcell 634 which serves as an enlarged flange region of the locking tab 632. The second subcell 634 preferably contains a tantalum radiopaque marker 625 press fit into the subcell 634 to facilitate visualization of the prostheses 600 under fluoroscopy. Radiopaque markers 625 may be press fit into any or all of the second subcells 634. Each curved strut 638 is attached to a zig-zag connector 639 which allows the prosthesis to flex in the radial direction relative to locking tab 632. The zig-zag connector is attached to a U-shaped connector 622. The two connections to U-shaped connectors 622 are separated by an intervening U-shaped connector. A space 642 is disposed between locking tabs 632, defined by a narrow inlet portion 643 and a wider receiver portion 645 adapted to receive the locking tab 632 from an adjacent prosthesis 600. Locking tabs 632 on the opposite end of prosthesis 600 are circumferentially offset with respect to the first end so that adjacent prostheses 600 may interleave and engage with one another. FIG. 6B illustrates how the ends of prostheses 600 with locking tabs 632 engage one another.

Figure 6C:
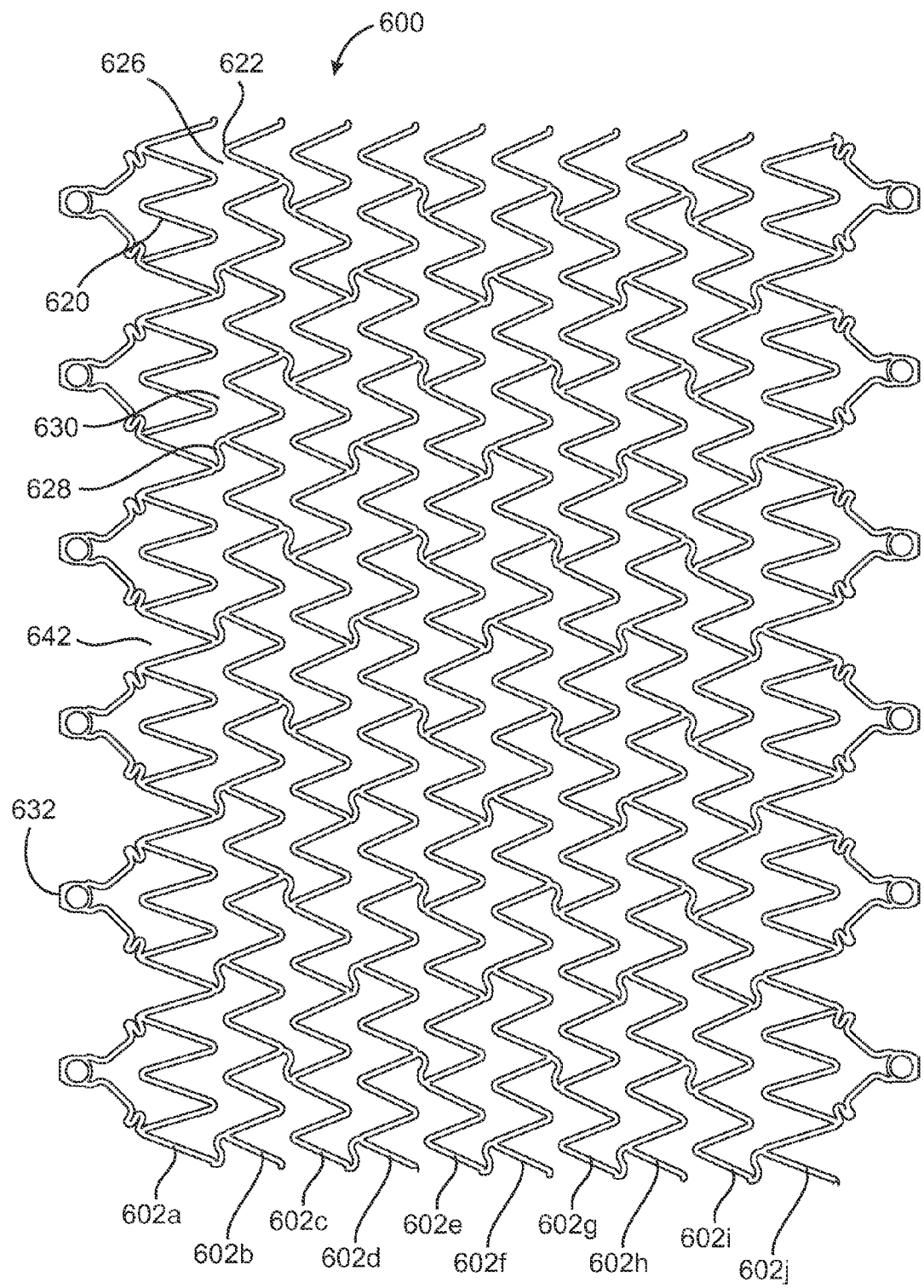
FIG. 6C illustrates a top view of the prosthesis shown in FIG. 6A after is has self-expanded.
Figure 6D:
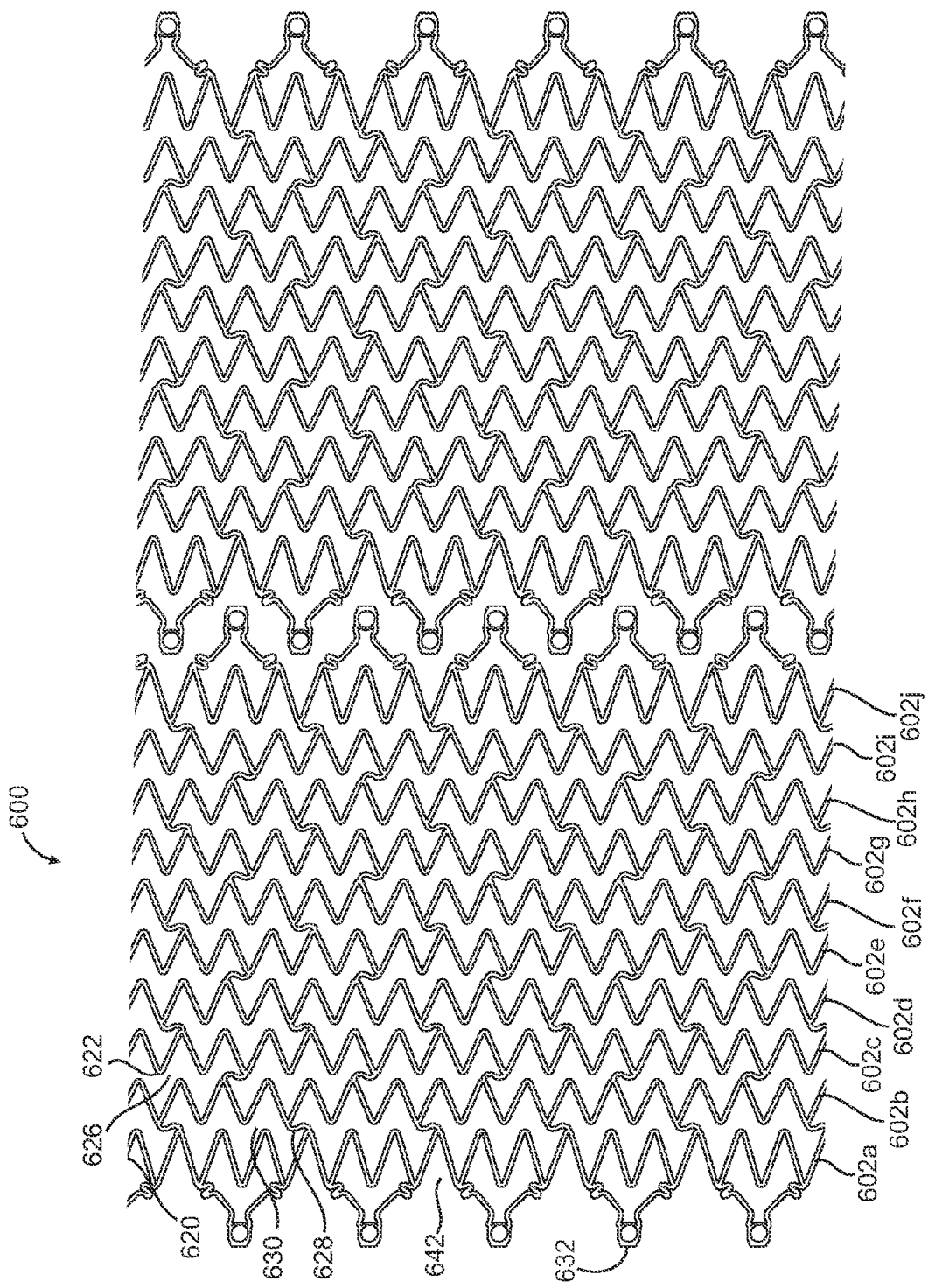
FIG. 6D shows the prosthesis of FIG. 6C adjacent to another prosthesis after both prostheses have been expanded.

FIG. 6C illustrates prosthesis 600 of FIGS. 6A-6B in the expanded configuration. After self-expanding, U-shaped connectors 622 deflect outwardly, expanding cells 626. Struts 620, while still substantially straight, are no longer horizontal and thus the period of the sinusoidal-like wave pattern forming each cell 626 increases and becomes more angular to form more of a zig-zag pattern, thereby increasing the diameter of the prosthesis 600. Cells 626 which originally appear as a series of horizontally oriented ovals, now appear as a series of triangles or offset diamonds. The radial expansion of prosthesis 600 also results in some foreshortening of the prosthesis 600 in the axial direction. Sigmoidal connectors 628 maintain the spacing 630 between columns of cells 618. Additionally, the space 642 between locking tabs 632 also expands circumferentially, thereby releasing the locking tab 632 on an adjacent prosthesis 600 after expansion. FIG. 6D illustrates two expanded prostheses 600 adjacent to one another after deployment. The interlocking tabs 632 have released but ends still interleave with one another, thereby providing better scaffolding of tissue in the area between adjacent stent segments.

FIG. 7A illustrates another embodiment of a prosthesis 700. Prosthesis 700 is similar to the embodiment shown in FIGS. 6A-6C, except that it has a different number of columns of open cells and the widths of the columns is different than disclosed for prosthesis 600 in FIGS. 6A-6C. Another difference is that connectors between columns 740a, 740b, 740c, 740d, 740e, 740f and 740g alternate between sloping upward and downward so that the left-most connector 740a between columns slopes in a first direction, here upward, and the right-most connector 740g between columns slopes in a second direction opposite of the first, here downward. Other structures in prosthesis 700 generally take the same form as described with respect to prosthesis 600 in FIGS. 6A-6C. Prosthesis 700 has eight columns of open cells, 702a, 702b, 702c, 702d, 702e, 702f, 702g and 702h. The proximal-most and distal-most column of cells, 702a and 702h are similar in width than the six inner columns of cells, 702b, 702c, 702d, 702e, 702f, 702g. Axial struts 704 which form the two outer columns 702a and 702b are therefore also similar in length to the axial struts 706 which form the other six columns of cells, 702b, 702c, 702d, 702e, 702f, 702g. Because struts 704 are similar in length to struts 706, the two outer columns of open cells 702a and 702b have a radial strength comparable to the six inner columns of open cells, 702b, 702c, 702d, 702e, 702f, 702g. Having consistent radial strength across prosthesis 700 may allow prosthesis 700 to self-expand more evenly during deployment as compared to other embodiments, thereby allowing more uniform vessel coverage. Having opposite sloping connectors 740a and 740g may aid in the rotational alignment of adjacent implanted stent segments. FIG. 7B illustrates how the ends of two adjacent prostheses 700 interlock with one another prior to deployment.

FIG. 8A illustrates yet another embodiment of a prosthesis 800. Prosthesis 800 is similar to the embodiment described in FIGS. 7A-7B. In this embodiment, the proximal-most and distal-most columns of open cells 804a and 804h have substantially the same length as the six other columns of open cells, 804b, 804c, 804d, 804e, 804f and 804g, thus columns 804a and 804g have a radial strength comparable to the six other columns 804b, 804c, 804d, 804e, 804f and 804g. The main difference between this embodiment and the embodiment of FIGS. 7A-7B is in the bridge connectors. Here, prosthesis 800 has two different bridge connectors, 806 and 814. Bridge connectors 814 are sigmoidal connectors between adjacent inner columns of open cells. Connectors 814 are arcuate because they connect a strut 812 in one column 804b with a strut 816 offset by two rows in the adjacent column of open cells, 804c. However, the connectors 806 that couple outer columns of open cells 804a and 804h with inner columns of open cells 804b and 804g are flatter and less arcuate. Connectors 806 are flatter because they connect a strut 808 in one column 804a with a strut 810 offset by a single row in the adjacent column of open cells, 804b. Additionally, interlocking tabs 820 form an aperture 802 that may hold a radiopaque marker. Also the space between interlocking tabs forms a surface 820 that is substantially transverse to the longitudinal axis of prosthesis 800 thereby allowing prosthesis 800 to be pushed in a direction that is substantially parallel to the longitudinal axis, minimizing tangential components of force. FIG. 8B illustrates two prostheses 800 interlocking with one another. This embodiment may also help control the prosthesis as it self-expands, thereby allowing more accurate deployment.

Other interleaving stent embodiments are described in copending U.S. patent application Ser. No. 10/738,666 filed Dec. 16, 2003; U.S. patent application Ser. No. 10/957,079 filed Sep. 30, 2004; and U.S. Provisional Application No. 60/784,309 filed Mar. 20, 2006, the entire contents of which are incorporated herein by reference.

Prostheses 128 are preferably composed of an elastic or superelastic shape memory alloy such as Nitinol so that the prostheses 128 resiliently self-expand upon release into a vessel by retraction of the sheath 124. Other possible materials include a spring temper metal such as stainless steel or cobalt-chromium so the prostheses 128 may be self-expanding in the body lumen at the target treatment site. In the case of self-expanding prostheses 128, an inflation balloon is not required but may still be used for predilation of a lesion or augmenting expansion of the self-expanding stent segments 128 (e.g. postdilation or tacking). Other materials such as biocompatible polymers may be used to fabricate prosthetic stent segments that self-expand, and these materials may further include bioabsorbable or bioerodable properties.

In other embodiments, prostheses 128 may have any of a variety of common constructions, such as but not limited to those described in U.S. patent application Ser. No. 10/738,666 filed Dec. 16, 2003, which was previously incorporated by reference. Constructions may include for example, closed cell constructions including expansible ovals, ellipses, box structures, expandable diamond structures, etc. In addition, the closed cells may have complex slotted geometries such as H-shaped slots, I-shaped slots, J-shaped slots, etc. Suitable open cell structures include zig-zag structures, serpentine structures, and the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337.

In preferred embodiments, prosthetic stent segments 128 may be coated, impregnated, infused or otherwise coupled with one or more drugs that inhibit restenosis, such as Rapamycin, Everolimus, Biolimus A9, Paclitaxel, analogs, prodrugs, or derivatives of the aforementioned, or other suitable agents, preferably carried in a durable or bioerodable carrier of polymeric or other suitable material. Alternatively, stent segments 128 may be coated with other types of drugs or therapeutic materials such as antibiotics, thrombolytics, antithrombotics, anti-inflammatories, cytotoxic agents, anti-proliferative agents, vasodilators, gene therapy agents, radioactive agents, immunosuppressants, chemotherapeutics, endothelial cell attractors or promoters and/or stem cells. Such materials may be coated over all or a portion of the surface of stent segments 128, or stent segments 128 may have a porous structure or include apertures, holes, channels, or other features in which such materials may be deposited.

Referring now to FIGS. 2A-2F, the deployment of selected prostheses to treat a lesion is shown in accordance with an exemplary embodiment. While the embodiment will be described in the context of a femoral artery stent procedure, it should be understood that the invention may be employed in any variety of peripheral or coronary arteries, blood vessels and other body lumens in which stents or tubular prostheses are deployed, including the carotid and iliac arteries, other arteries or veins, as well as non-vascular body lumens, such as the ureter, urethra, fallopian tubes, the hepatic and biliary duct and the like. The delivery catheter is introduced into a treatment vessel first, by placing an introducer sheath (not illustrated) into the target peripheral artery, typically using a percutaneous procedure such as the Seldinger technique or by surgical cutdown. In this exemplary embodiment, the target vessel is a femoral artery. The introducer sheath is then advanced slightly into the femoral artery. A guidewire GW is then inserted through the introducer and advanced into the target vessel V where a lesion L to be treated is located. The proximal end of guidewire GW is then inserted through distal port 256 of nosecone 236 and through guidewire tube 122 (FIG. 1A) which is outside the patient's body. Optionally, a guide catheter may also be employed.

FIG. 2A shows a stent delivery catheter 200 slidably advanced over the guidewire GW into the vessel V so that nosecone 236 is distal to the lesion L. Self-expanding tubular prostheses 228 having ends in engagement with one another, as shown in FIG. 4B, are disposed over inner shaft 234 and a radially expandable control member 230. The prostheses 228 are also covered by outer sheath 224. In this embodiment, eight prostheses 228 are carried by the stent delivery catheter 200, although only five can be seen in FIG. 2A.

Outer sheath 224 has a high hoop strength near the distal end (but proximal to the expandable tip if any) such that the outer sheath 224 is able to prevent the self-expanding prostheses 228 from expanding when the outer sheath 224 is disposed thereover. The outer sheath 224 also prevents the radially expandable control member 230 from expanding. This may be accomplished by using an outer sheath 224 with a suitable wall thickness or the sheath 224 may also have a distal portion formed from a metal or polymer reinforced with a metallic or polymeric braid to resist radial expansion of the self-expanding prostheses 228 and control member 230. In preferred embodiments, the entire length of sheath 224 may be reinforced.

In this embodiment, each prosthesis 228 has a length approximately 20 mm long. Thus the delivery catheter 200 is adapted to deliver a prosthesis having a total length from about 20 mm long, up to 160 mm long, in 20 mm increments. Other lengths and quantities of prostheses 228 may be employed and this exemplary embodiment is not meant to limit the scope of the present invention.

Radiopaque marker band 252 on sheath 224 is disposed near the distal end of outer sheath 224 and helps an operator to visualize the delivery catheter tip under fluoroscopy as well as assisting the operator in determining lesion length. In preferred embodiments, although not required, the outer sheath also comprises an expandable distal tip 254 which is adapted to expand with the prostheses 228 as they self-expand. A preferred embodiment of the flexible tip 254 is illustrated in FIGS. 5A-5B.

Referring now to FIG. 5A, a delivery catheter 500 has an outer sheath 502. The distal tip of outer sheath 502 comprises a plurality of axial slits defining a plurality of deflectable sections or petals 506. The tips of sections 506 are disposed within an aperture on the proximal end of nosecone 508. In alternative embodiments, instead of axial slits, the outer sheath may have a resilient distal tip that is capable of expanding and contracting. The tip may be fabricated from a resilient elastomer such as silicone, latex or other rubber-like materials. The outer sheath 502 also may comprise a reinforced region 504 near the distal sheath end. This reinforced region 504 may be formed by bonding a polymeric sleeve to the outer sheath 502. FIG. 5B shows how the distal tip of outer sheath 506 expands during prosthesis deployment. In FIG. 5B, outer sheath 502 is retracted proximally, pulling the outer sheath tip 502 away from nosecone 508 and also exposing radially expandable control member 510. Radially expandable control member 510 comprises a plurality of resilient axial struts 511 which self-expand outwardly to form a wire-like basket once unconstrained. The resilient axial struts 511 are often formed from superelastic nickel-titanium alloys such as Nitinol, spring temper stainless steel or polymers with a preset shape may be used. The struts 511 may have any number of geometries such as round, square, oval or rectangular cross-sections and the struts are elongate and wire-like. Often, struts 511 are formed by slitting a tube. Retracting outer sheath 502 allows a prosthesis (not shown) to self-expand which in turn causes the distal tip 506 of outer sheath 502 to flex outwardly forming a plurality of sections 506. Additionally, retraction of sheath 502 also allows the radially expandable control member 510 to expand. Four to eight petals may be used, although preferably six petals are used. The prosthesis (not shown) is therefore trapped between the petals 506 of the flexible sheath tip and the radially expandable control member 510, which controls prosthesis axial movement during deployment.

Referring back to FIG. 2A, radially expandable control member 230 is disposed initially under prostheses 228 and expands with the distal-most prosthesis 228 as it self-expands. Once expanded, radially expandable control member 230 forms a wire-like basket. The radially expandable control member 230 controls axial position of prostheses 228 relative to catheter 200 during their deployment and therefore allows precise placement and spacing of the prostheses 228 at the site of a lesion, L. Additionally, a pusher tube 144 (seen in FIG. 1C) is axially disposed along the inner shaft 234 and serves as a backstop to prevent proximal motion of prostheses 228. Additional details on these elements will be discussed in greater detail below, with respect to FIGS. 2B-2F.

Referring now to FIG. 2B, the lesion L to be treated is typically visualized by introducing contrast media into the target vessel V and observing the resulting image under a fluoroscope. Radiopaque marker 252 near the distal end of outer sheath 224 is used to help visualize the position of the delivery catheter 200 relative to the lesion L as well as to visualize the length of prostheses 228 exposed for deployment relative to the target lesion L. In alternative embodiments, radiopaque markers may be disposed on the prosthesis as discussed previously with reference to FIGS. 6A-6B. Positioning is accomplished by advancing the delivery catheter so that radiopaque marker 252 is near the distal edge of the lesion L and then outer sheath 224 is retracted until radiopaque marker 252 is near the proximal edge of the lesion L. Retraction of outer sheath 224 is accomplished using a control mechanism such as slider 102 in FIG. 1A which exposes prostheses 228 and removes the constraint provided by outer sheath 224 allowing the prostheses 228 to expand into and cover the lesion L, as seen in FIG. 2B. A pusher tube 144 (FIG. 1C) acts as a backstop and prevents proximal motion of the prostheses 228 during retraction of the outer sheath 224.

In FIG. 2B as outer sheath 224 is retracted, a distal-most prosthesis 260 becomes unconstrained and self-expands into engagement with the lesion L. As the prosthesis 260 self-expands, radially expandable control member 230 disposed under the prostheses 228 also expands and engages an inner surface of the prosthesis 260, thereby urging the prosthesis 260 against the inner surface of outer sheath 224. The radially expandable control member 230 forms a wire-like basket in its expanded shape which compresses the prosthesis 260 against the sheath 224. In a preferred, yet optional embodiment, outer sheath 224 also comprises an expandable distal tip 254 which conforms to the expanded shape of control member 230 and provides a flared interior against which the prosthesis may be trapped. Trapping the prosthesis 260 between the radially expandable control member 230 and the outer sheath 224 prevents it from jumping away from the delivery catheter and thus the prosthesis 260 may be precisely placed in the treatment vessel V at the side of a lesion L. Optionally, the control member 230 may be held in traction to further "clamp" the prosthesis 260 between the control member 230 and the sheath 224. One or ordinary skill in the art will also appreciate the pusher tube 144 may also be used to engage and retract a prosthesis that has been partially deployed but that is still partially constrained by sheath 224, in order to retrieve the prosthesis and prevent it from being deployed.

Referring now to FIG. 2C, if additional prostheses 228 are required to fully traverse the length of the lesion L, outer sheath 224 is further retracted proximally using the slider 102 on handle 106 of FIG. 1A, thereby exposing an additional prosthesis 262. Once the constraint provided from the outer sheath 224 has been removed from prosthesis 262, it self-expands into the lesion L. Radially expandable control member 230 is operably coupled with outer sheath 224, therefore, as outer sheath 224 is retracted proximally, radially expandable control member 230 also retracts in conjunction with outer sheath 224. As radially expandable control member 230 is retracted proximally, it disengages from the distal nose cone 236 and as prosthesis 262 self-expands, it is trapped between the radially expandable control member 230 and the flexible distal tip of outer sheath 224. In alternative embodiments, the radially expandable control member 230 may be offset axially away from nose cone 236 and thus control member 230 simply expands as outer sheath 224 is retracted. This prevents the prosthesis 262 from jumping axially so that it may be delivered precisely into the lesion L and adjacent to the first prosthesis 260. In alternative embodiments, the wire-like basket 230 which serves as a radially expandable control member may also remain stationary after its initial deployment within the distal-most prosthesis 260. This embodiment is disclosed in co-pending U.S. patent application Ser. No. 10/944,282 filed Sep. 17, 2004, the entire contents of which are incorporated herein by reference.

Referring now to FIG. 2D, the process of exposing prostheses 262 so they may self-expand into the lesion is repeated until the entire lesion is traversed by prostheses 260. In FIG. 2D, outer sheath 224 is retracted further proximally along with radially expandable control member 230. Additional prostheses 262 are controllably deployed from the delivery catheter 200. Prostheses 262 are deployed so that their ends are adjacent to one another without overlapping.

Figure 2E:
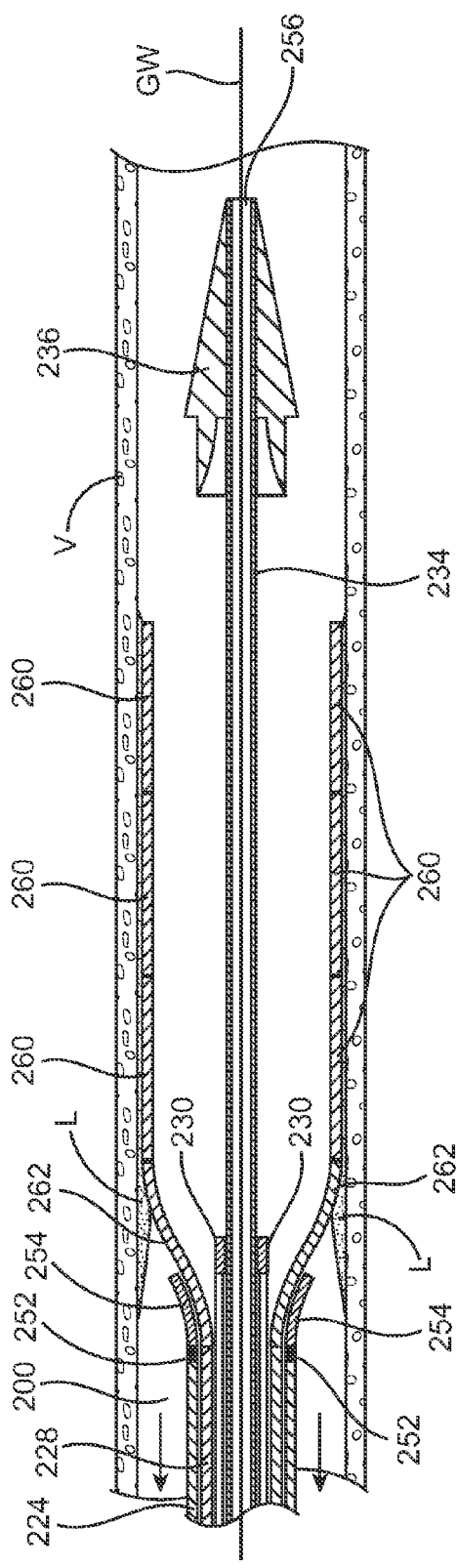
Figure 2F:
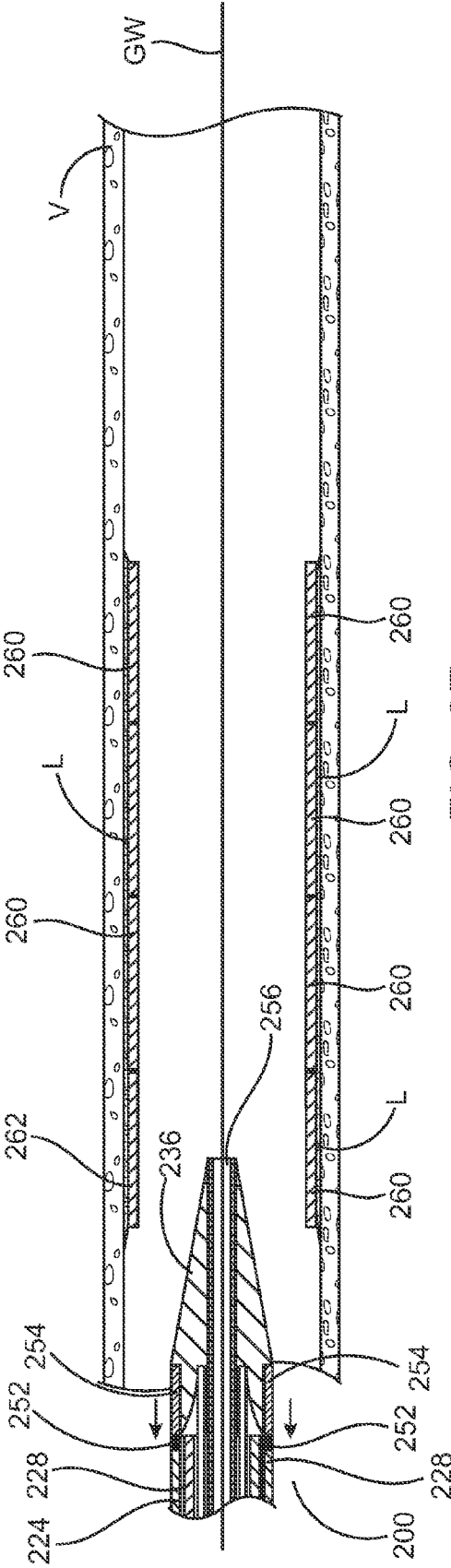

Referring now to FIG. 2E, the last prosthesis 262 is deployed. By visualizing radiopaque marker 252 near the proximal end of the lesion L under fluoroscopy, the operator knows that no further prostheses 228 are required to cover lesion L. After outer sheath 224 has been withdrawn proximally enough to deploy the last prosthesis 262, radially expandable control member 230 is collapsed by retracting it into the delivery catheter 200, using the slider control 140 on handle 106 of FIG. 1A. Delivery catheter 200 may then be proximally withdrawn from the lesion. Inner shaft 234 may then be retracted into sheath 224 as seen in FIG. 2F, repositioning prostheses 262 distally up to nosecone 236. Delivery catheter 200 can then be removed from the vessel being treated or repositioned to a new treatment site for deployment of additional prostheses 228.

FIGS. 3A-3D illustrate the deployment of selected prosthetic segments to treat a lesion in another exemplary embodiment. This embodiment is similar to that previously discussed, however a significant difference is the replacement of the wire-like basket 230 in FIGS. 2A-2E with an expandable balloon serving as the radially expandable control member. As discussed above, this embodiment will be described in the context of a femoral artery stent procedure, but this is not intended to limit the invention which may be employed in any variety of blood vessels and other body lumens in which stents or tubular prostheses are deployed.

Referring now to FIGS. 3A-3D, the deployment of selected prostheses to treat a lesion is shown in accordance with an exemplary embodiment. The delivery catheter 300 is introduced into a treatment vessel as previously described.

FIG. 3A shows a stent delivery catheter 300 slidably advanced over the guidewire GW into the vessel V so that nosecone 336 is distal to the lesion L. Self-expanding tubular prostheses 328 having ends in engagement with one another, as shown in FIG. 4B, are disposed over inner shaft 334 and a radially expandable control member 330, here a balloon. The balloon 330 may be formed from a semi-compliant polymer such as Pebax, Nylon, polyurethane, polypropylene, PTFE or other suitable polymers. Compliant balloons formed from latex and silicone may also be used. The prostheses 328 are also covered by outer sheath 324. In this embodiment, eight prostheses 328 are carried by the stent delivery catheter 300, although various numbers are possible.

Outer sheath 324 has a high hoop strength near the distal end such that the outer sheath 324 is able to prevent the self-expanding prostheses 328 from expanding when the outer sheath 324 is disposed thereover. This may be accomplished by using an outer sheath 324 with a thicker wall or the sheath 324 may also have a distal portion formed from a metal or polymer reinforced with a metallic or polymeric braid to resist radial expansion of the self-expanding prostheses 328. The entire length of sheath 324 may also be reinforced.

In this embodiment, each prosthesis 328 has a length approximately 20 mm long. Thus the delivery catheter 300 is adapted to deliver a prosthesis having a total length from about 20 mm long, up to 160 mm long, in 20 mm increments. Other lengths and quantities of prostheses 328 may be employed and this exemplary embodiment is not meant to limit the scope of the present invention.

Radiopaque marker band 352 disposed near the distal end of outer sheath 324 helps to visualize the delivery catheter tip under fluoroscopy as well as assisting the operator in determining lesion length. In preferred embodiments, although not required, the outer sheath also comprises a soft flexible distal tip 354 which is adapted to expand with the prostheses 328 as they self-expand. A preferred embodiment of the flexible tip 354 is illustrated in FIGS. 5A-5B and has previously been discussed.

In FIG. 3A, a balloon 330 is the radially expandable control member. Balloon 330 is disposed under prostheses 328 and expands with prostheses 328 as they self-expand. Control member 330 may be actively inflated or passively inflated. For example the balloon 330 may be coupled with a constant pressure source, thus once sheath 324 is retracted and prostheses 328 begin to expand, constraint from balloon 330 is removed. The constant pressure source will therefore automatically inflate balloon 330 until it engages the expanded prostheses 328. Alternatively, an operator may manually inflate balloon 330 as sheath 324 is retracted. A fluid such as contrast media and/or saline may be used to inflate balloon 330. The fluid is delivered to balloon 330 via a lumen (not illustrated) in inner shaft 334 coupled with an adapter such as a Luer connector on the proximal end of inner shaft 334. Once expanded, radially expandable control member 330 forms an inflated balloon. The balloon 330 constrains the axial movement of prostheses 328 during their deployment and therefore allows precise placement of the prostheses 328 into the target vessel V at the site of a lesion, L. Additionally, a pusher tube 144 (seen in FIG. 1C) is axially disposed along the inner shaft 334 and serves as a backstop to prevent proximal motion of prostheses 328. Additional details on these elements will be discussed in greater detail below, with respect to FIGS. 3B-3D.

Referring now to FIG. 3B, the length of the lesion L to be treated is typically visualized by introducing contrast media into the target vessel V and observing the resulting image under a fluoroscope. Radiopaque marker 352 near the distal end of outer sheath 324 is used to help visualize the position of the delivery catheter 300 relative to the lesion L as well as to visualize the length of prostheses 328 exposed for deployment relative to the target lesion L. Positioning is accomplished by advancing the delivery catheter so that radiopaque marker 352 is near the distal edge of the lesion L and then outer sheath 324 is retracted until radiopaque marker 352 is near the proximal edge of the lesion L. Retraction of outer sheath 324 is accomplished using a control mechanism such as slider 102 in FIG. 1A which exposes prostheses 328 and removes the constraint provided by outer sheath 324 allowing the prostheses 328 to expand into and cover the lesion L, as seen in FIG. 3B.

In FIG. 3B as outer sheath 324 is retracted a distal-most prosthesis 360 becomes unconstrained and self-expands into engagement with the lesion L. A radially expandable control member 330, here a balloon, disposed under the prostheses 328 is inflated via adapter 108 on the proximal end of handle 106 so as to expand within the prosthesis 360. A constant pressure source may be employed as an active means for ensuring uniform balloon expansion as sheath 324 is retracted. Alternatively, passive balloon inflation may be employed and the balloon 330 may be manually inflated by an operator. The balloon control member 330 engages an inner surface of the prosthesis 360, thereby urging the prosthesis 360 against outer sheath 324. In a preferred, yet optional embodiment, outer sheath 324 also has an expandable distal tip 354 that was previously described above with respect to FIGS. 5A-5B. Capturing the prosthesis 360 between the radially expandable control member 330 and the outer sheath 324 prevents it from jumping away from the delivery catheter and thus the prosthesis 360 may be precisely placed in the treatment vessel V at the side of a lesion L.

Referring now to FIG. 3C additional prostheses 360 are deployed from the delivery catheter 300 to the lesion L. In FIG. 3C, the first prosthesis 360 has been deployed into the lesion L. Additional prostheses 328 are required to fully traverse the length of the lesion L, therefore in FIG. 3C, outer sheath 324 is further retracted proximally using the slider 102 on handle 106 of FIG. 1A, thereby exposing an additional prosthesis 362. The prostheses 328 are prevented from moving in the proximal direction by a pusher tube 144 (FIG. 1C) which acts as a backstop. Once the constraint provided from the outer sheath 324 has been removed from prosthesis 362, it self-expands into the lesion L. Radially expandable control member 330 is operably coupled with outer sheath 324, therefore, as outer sheath 324 is retracted proximally, radially expandable control member 330 also retracts with outer sheath 324. As radially expandable control member 330 is retracted proximally, it disengages from the distal nose cone 336 and as prosthesis 362 self-expands, it is trapped or compressed between the radially expandable control member 330 and the flexible distal tip of outer sheath 324. Trapping the prosthesis 362 in this way controls its axial position so that it may be delivered precisely into the lesion L and adjacent to the first prosthesis 360. In some embodiments, the radially expandable control member 330 may remain stationary within the distal-most prosthesis 360 and control member 330 does not move proximally with the outer sheath 324. Aspects of such embodiments are disclosed in co-pending U.S. patent application Ser. Nos. 10/957,079 filed Sep. 30, 2004; 10/879,949 filed Jun. 28, 2004 and 10/944,282 filed Sep. 17, 2004, the entire contents of which have previously been incorporated by reference.

Referring now to FIG. 3D, the process of exposing prostheses 362 so they may self-expand into the lesion is repeated until the entire lesion is traversed by prostheses 360. In FIG. 3D, outer sheath 324 is retracted further proximally along with radially expandable control member 330. Additional prostheses 362 are controllably deployed from the delivery catheter 300. Prostheses 362 are deployed so that their ends are adjacent to one another without overlapping.

After the last prosthesis 328 has been deployed into the lesion, as indicated when radiopaque marker 352 is near the proximal end of the lesion L, as seen under a fluoroscope, the balloon 330 may be deflated and the exposed balloon length adjusted by advancing or retracting sheath 324. Once the exposed balloon length has been adjusted, the balloon may be reinflated and an optional post dilation or "tacking" of the stent may be performed. The radially expandable control member 330 is then retracted from the deployed prostheses 360 by deflating the balloon 330. The delivery catheter 300 is then withdrawn proximally away from the lesion. Inner shaft 334 may then be retracted into sheath 324, repositioning prostheses 328 distally, up to nosecone 336. Delivery catheter 300 may then be withdrawn from the vessel being treated or repositioned to a new treatment site for deployment of additional prostheses 328.

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A catheter for delivering a prosthesis to a treatment site in a body lumen, the catheter comprising:
   a pusher tube having a proximal end and a distal end;
   a sheath slidably disposed over the pusher tube;
   one or more self-expanding tubular prostheses carried within the sheath which constrains the prostheses in a radially contracted configuration, the one or more prostheses being independently releasable from the sheath as the sheath is retracted relative to the pusher tube, the prostheses resiliently expanding upon release from the sheath; and
   a radially expandable control member positionable within the prostheses and disposed over an elongate flexible member having a lumen therethrough that is adapted to receive a guidewire, the control member having an expanded shape which engages an inner surface of at least one of the prostheses to exert an outward force against the at least one prosthesis, the control member comprising a plurality of elongate struts having an arcuate configuration in the expanded shape, the control member being axially movable with the sheath and proximally movable relative to the elongate flexible member while in the expanded shape so as to slide relative to the prostheses in engagement therewith as the sheath is retracted relative to the pusher tube,
   wherein the pusher tube is adapted to prevent proximal motion of the one or more self-expanding prostheses as the sheath is retracted.

2. The catheter of claim 1 wherein the control member urges the prosthesis outwardly against the sheath.

3. The catheter of claim 1, wherein the control member urges the prosthesis outwardly against an interior surface of the sheath.

4. The catheter of claim 1, wherein the plurality of elongate struts are disposed distal to the pusher tube.

5. The catheter of claim 1, wherein the radially expandable control member expands with a distal-most prosthesis as the distal-most prosthesis expands.

6. The catheter of claim 1, wherein the expandable member is a metal.

7. The catheter of claim 1, wherein the plurality of elongate struts form a basket.

8. The catheter of claim 7, wherein at least some of the plurality of elongate struts are oriented axially and bend outwardly under compression.

9. The catheter of claim 7, wherein the plurality of elongate struts are metal.

10. The catheter of claim 7, wherein the plurality of elongate struts are a polymer.

11. The catheter of claim 1, wherein the expandable member is a polymer.

12. The catheter of claim 1, wherein the self-expanding tubular prostheses carry a therapeutic agent adapted to being released therefrom.

13. The catheter of claim 12, wherein the therapeutic agent comprises an anti-restenosis agent.

14. The catheter of claim 1, wherein the radially expandable control member engages at least two self-expanding prostheses simultaneously.

15. The catheter of claim 1, further comprising a handle near the proximal end of the pusher tube, the handle having a control mechanism adapted to actuate the sheath and the radially expandable control member during deployment of the self-expanding prostheses.

16. The catheter of claim 15, wherein the sheath is adapted to be retracted while the pusher tube remains fixed relative to the handle so as to expose at least one of the self-expanding tubular prostheses for deployment.

17. The catheter of claim 1, wherein the sheath has a radially expandable distal tip interactive with the control member disposed distally of the distal tip to enable a self-expanding prosthesis to be trapped therebetween to inhibit the prosthesis from jumping distally upon expansion.

18. The catheter of claim 17, wherein the distal tip is flared.

19. The catheter of claim 17, wherein the distal tip is expandable as the prosthesis expands.

20. The catheter of claim 17, wherein the distal tip has a plurality of tines arranged in a cylindrical pattern and extending distally from a distal end of the sheath.

21. The catheter of claim 1, wherein the one or more self-expanding prostheses comprise a plurality of self-expanding prostheses.

22. The catheter of claim 21, wherein the self-expanding tubular prostheses have a length in the range of about 2 mm to about 50 mm.

23. The catheter of claim 21, wherein each of the self-expanding prostheses have the same length.

24. The catheter of claim 21, wherein at least one of the self-expanding prostheses has a length different than at least another of the self-expanding prostheses.

25. The catheter of claim 21, wherein the self-expanding prostheses have ends in engagement with one another prior to deployment.

26. The catheter of claim 21, wherein the self-expanding prostheses are axially connected to each other when in the sheath.

27. The catheter of claim 1, wherein the pusher tube is proximal to the self-expanding prostheses.

28. The catheter of claim 1, wherein the pusher is adapted to engage a prosthesis in the sheath for retrieval thereof, thereby preventing the prosthesis from being deployed.

29. The catheter of claim 1, wherein the elongate flexible member is disposed at least partially under the pusher tube.

30. The catheter of claim 29, wherein the one or more prostheses comprise a plurality of self-expanding prostheses.

31. The catheter of claim 30, wherein the self-expanding tubular prostheses have a length in the range of about 2 mm to about 50 mm.

32. The catheter of claim 30, wherein each of the self-expanding prostheses have the same length.

33. The catheter of claim 30, wherein at least one of the self-expanding prostheses has a length different than at least another of the self-expanding prostheses.

34. The catheter of claim 30, wherein the self-expanding prostheses have ends in engagement with one another prior to deployment.

35. The catheter of claim 30, wherein the prostheses are axially connected when in the sheath.

36. A catheter for delivering a prosthesis to a treatment site in a body lumen, the catheter comprising:
a pusher tube having a proximal end and a distal end;
a sheath slidably disposed over the pusher tube and having a distal tip;
one or more self-expanding tubular prostheses carried within the sheath which constrains the prostheses in a radially contracted configuration, the one or more prostheses being independently releasable from the sheath as the sheath is retracted relative to the pusher tube, the prosthesis resiliently expanding upon release from the sheath; and
a radially expandable control member positionable within the prostheses and disposed over an elongate flexible member having a lumen therethrough that is adapted to receive a guidewire, the control member having an expanded shape which engages an inner surface of at least one of the prostheses to exert an outward force against the at least one prosthesis so as to urge the prosthesis outwardly against the sheath, the control member comprising a plurality of elongate struts having an arcuate configuration in the expanded shape and the control member being axially movable with the sheath and proximally movable relative to the elongate flexible member while in the expanded shape so as to slide relative to the prosthesis in engagement therewith as the sheath is refracted relative to the pusher tube,
wherein the distal tip of the sheath is interactive with the control member to enable a prosthesis to be trapped therebetween to inhibit the prosthesis from jumping distally upon expansion, and
wherein the pusher tube is adapted to prevent proximal motion of the one or more self-expanding prostheses as the sheath is retracted.

37. The catheter of claim 36, wherein the distal tip is flared.

38. The catheter of claim 36, wherein the distal tip is expandable as the prostheses expand.

39. The catheter of claim 36, wherein the distal tip has a plurality of tines arranged in a cylindrical pattern and extending distally from a distal end of the sheath.

40. The catheter of claim 36, wherein the control member urges the prosthesis outwardly against an interior surface of the sheath.

41. The catheter of claim 36, wherein the plurality of elongate struts are disposed distal to the pusher tube.

42. The catheter of claim 41, wherein the struts are resilient and bend outwardly under compression.

43. The catheter of claim 36, wherein the expandable member is a metal.

44. The catheter of claim 36, wherein the plurality of elongate struts form a basket.

45. The catheter of claim 44, wherein at least some of the plurality of elongate struts are oriented axially and bend outwardly under compression.

46. The catheter of claim 44, wherein the plurality of elongate struts are metal.

47. The catheter of claim 44, wherein the plurality of elongate struts are a polymer.

48. The catheter of claim 36, wherein the expandable member is a polymer.

49. The catheter of claim 36, wherein the self-expanding tubular prostheses carry a therapeutic agent adapted to being released therefrom.

50. The catheter of claim 49, wherein the therapeutic agent comprises an anti-restenosis agent.

51. The catheter of claim 36, wherein the radially expandable control member engages at least two self-expanding prostheses simultaneously.

52. The catheter of claim 36, further comprising a handle near the proximal end of the pusher tube, the handle having a control mechanism adapted to actuate the sheath and the radially expandable control member during deployment of the self-expanding prostheses.

53. The catheter of claim 52, wherein the sheath is adapted to be retracted while the pusher tube remains fixed relative to the handle so as to expose at least one of the self-expanding tubular prostheses for deployment.

54. The catheter of claim 36, wherein the pusher tube is proximal to the self-expanding prostheses.

55. The catheter of claim 54, wherein the pusher is adapted to engage a prosthesis in the sheath for retrieval thereof, thereby preventing the prosthesis from being deployed.

56. The catheter of claim 36, further comprising an wherein the elongate flexible member is disposed at least partially under the pusher tube.

57. A method of delivering a prosthesis to a treatment site in a body lumen, the method comprising:
positioning a delivery catheter at the treatment site, the delivery catheter having one or more self-expanding tubular prostheses thereon and covered by a sheath;
retracting the sheath so as to expose the prosthesis, the prosthesis resiliently expanding radially into contact with a wall of the body lumen;
radially expanding a control member slidably coupled to the delivery catheter;
engaging an interior surface of the prosthesis with the control member as the sheath is retracted, the control member being positioned distally of the sheath and retracted in conjunction with the sheath and exerting an outward force against the prosthesis to maintain the axial position of the prosthesis relative to the delivery catheter as the prosthesis is released from the sheath; and
releasing the self-expanding tubular prosthesis from the delivery catheter into the body lumen.

58. The method of claim 57, wherein the control member urges the prosthesis outwardly against the sheath.

59. The method of claim 57, wherein releasing the prosthesis comprises collapsing the radially expandable control member so that the radially expandable control member disengages from the inner surface of the prosthesis.

60. The method of claim 57, wherein the radially expandable control member comprises a plurality of elongate wire-like struts axially oriented and adapted to bend outwardly under compression.

61. The method of claim 57, wherein the delivery catheter carries a plurality of self-expanding tubular prostheses.

62. The method of claim 61, wherein the plurality of self-expanding tubular prostheses are releasably interconnected while disposed on the delivery catheter.

63. The method of claim 62, wherein the prostheses disconnect upon expansion.

64. The method of claim 57, further comprising retracting the control member axially in conjunction with the sheath so as to slide relative to the prosthesis in engagement therewith.

65. The method of claim 57, wherein at least some of the self-expanding tubular prostheses carry a therapeutic agent adapted to being released therefrom.

66. The method of claim 65, wherein the therapeutic agent comprises an anti-restenosis agent.

67. The method of claim 57, wherein at least another self-expanding prosthesis is retained in the sheath after the prosthesis is released.

68. The method of claim 57, wherein a distal end of the sheath radially expands as the self-expanding prostheses expand.

69. The method of claim 68, wherein the distal end of the sheath flares outwardly as the self-expanding prostheses expand.

70. The method of claim 68, wherein the distal end of the sheath is axially split into sections, the sections deflecting outwardly as the self-expanding prostheses expand.

71. The method of claim 68, wherein the distal end of the sheath resiliently returns to a non-expanded shape following release of the desired number of self-expanding prostheses.

72. The method of claim 68, wherein the distal end of the sheath resiliently returns to a non-expanded shape following retraction of the control member into the sheath.

73. The method of claim 68, wherein the distal end of the sheath is radially expanded by an outward force exerted by the control member.

74. The method of claim 68, wherein the distal end of the sheath is radially expanded by an outward force exerted by the self-expanding prostheses.

* * * * *

UNITED STATES PATENT AND TRADEMARK OFFICE
CERTIFICATE OF CORRECTION

PATENT NO. : 8,317,859 B2
APPLICATION NO. : 11/752448
DATED : November 27, 2012
INVENTOR(S) : David W. Snow et al.

It is certified that error appears in the above-identified patent and that said Letters Patent is hereby corrected as shown below:

In the Claims:

Column 23, line 33, please delete "refracted" and insert --retracted--.

Signed and Sealed this
Nineteenth Day of March, 2013

Teresa Stanek Rea
*Acting Director of the United States Patent and Trademark Office*